United States Patent
Vuyk, Jr.

(10) Patent No.: US 12,276,077 B2
(45) Date of Patent: Apr. 15, 2025

(54) METHODS AND APPARATUS FOR FOUNDATION MONITORING

(71) Applicant: Vuyk Technology Holdings, LLC, Cypress, TX (US)

(72) Inventor: Adrian Vuyk, Jr., Cypress, TX (US)

(73) Assignee: Vuyk Technology Holdings, LLC, Cypress, TX (US)

(*) Notice: Subject to any disclaimer, the term of this patent is extended or adjusted under 35 U.S.C. 154(b) by 482 days.

(21) Appl. No.: 17/586,085

(22) Filed: Jan. 27, 2022

(65) Prior Publication Data
US 2022/0235532 A1 Jul. 28, 2022

Related U.S. Application Data

(60) Provisional application No. 63/145,210, filed on Feb. 3, 2021, provisional application No. 63/142,105, filed on Jan. 27, 2021.

(51) Int. Cl.
*E02D 33/00* (2006.01)
*E02D 1/02* (2006.01)
(Continued)

(52) U.S. Cl.
CPC .............. *E02D 33/00* (2013.01); *E02D 1/02* (2013.01); *E02D 1/08* (2013.01); *G01K 13/00* (2013.01);
(Continued)

(58) Field of Classification Search
CPC .. E02D 33/00; E02D 1/02; E02D 1/08; E02D 2600/10; G01K 13/00; G01L 19/0092; G01L 19/086; G01N 33/24; G01N 33/383
See application file for complete search history.

(56) References Cited

U.S. PATENT DOCUMENTS

| 4,003,263 A | 1/1977 | O'Rourke |
| 4,073,114 A | 2/1978 | Yish |

(Continued)

FOREIGN PATENT DOCUMENTS

| CN | 101446486 A | * | 6/2009 |
| CN | 104950921 A | | 9/2015 |

(Continued)

OTHER PUBLICATIONS

CN-101446486-A, English Translation (Year: 2009).*

(Continued)

*Primary Examiner* — Ryan D Walsh
(74) *Attorney, Agent, or Firm* — Patterson + Sheridan, LLP

(57) ABSTRACT

A system for monitoring a foundation includes a sensor cartridge assembly. The sensor cartridge assembly includes a sensor disposed in a sensor tube and a sensor head attached to an end of the sensor tube. Wiring coupled to the sensor and routed in the sensor tube to the sensor head conveys power and/or telemetry between the sensor and a controller. The sensor tube is configured to be inserted into a raceway attached to a foundation. The raceway may be within the foundation and/or located at a perimeter of the foundation. A method for monitoring a foundation includes deriving an elevation of the foundation at the location of the sensor based on pressure measurements made by the sensor within the sensor tube.

13 Claims, 16 Drawing Sheets

(51) Int. Cl.
  *E02D 1/08* (2006.01)
  *G01K 13/00* (2021.01)
  *G01L 19/00* (2006.01)
  *G01L 19/08* (2006.01)
  *G01N 33/24* (2006.01)
  *G01N 33/38* (2006.01)

(52) U.S. Cl.
  CPC ........ *G01L 19/0092* (2013.01); *G01L 19/086* (2013.01); *G01N 33/24* (2013.01); *G01N 33/383* (2013.01); *E02D 2600/10* (2013.01)

(56) References Cited

U.S. PATENT DOCUMENTS

| | | | |
|---|---|---|---|
| 4,137,527 | A | 1/1979 | Tennehouse et al. |
| 4,231,163 | A | 11/1980 | Turloff |
| 4,673,315 | A | 6/1987 | Shaw |
| 5,337,613 | A | 8/1994 | Kovari |
| 5,367,782 | A | 11/1994 | Zumitani |
| 10,087,596 | B2 | 10/2018 | Vuyk, Jr. et al. |
| 10,526,763 | B2 | 1/2020 | Conner et al. |
| 11,414,859 | B2 | 8/2022 | Houston |
| 11,438,740 | B2 | 9/2022 | Hill et al. |
| 11,585,066 | B2 | 2/2023 | Marawi et al. |
| 2004/0153270 | A1* | 8/2004 | Yamashita ........... G01N 33/383 702/81 |
| 2005/0072067 | A1 | 4/2005 | Wobben |
| 2006/0021447 | A1 | 2/2006 | Hecht et al. |
| 2008/0061959 | A1 | 3/2008 | Breed |
| 2010/0006161 | A1 | 1/2010 | Rothleitner |
| 2010/0095603 | A1 | 4/2010 | Defilipp |
| 2010/0238020 | A1* | 9/2010 | Pellen .................. H01B 7/324 340/533 |
| 2011/0203370 | A1 | 8/2011 | Argov |
| 2011/0238452 | A1 | 9/2011 | Ziade et al. |
| 2011/0295523 | A1 | 12/2011 | Hovhanessian et al. |
| 2015/0276702 | A1 | 10/2015 | England |
| 2018/0100282 | A1 | 4/2018 | Vuyk, Jr. et al. |
| 2019/0145249 | A1* | 5/2019 | Provenzano ........... G01D 21/02 73/152.52 |
| 2020/0072605 | A1* | 3/2020 | Breton .................. G01L 13/00 |
| 2020/0354917 | A1 | 11/2020 | Conner et al. |
| 2022/0417715 | A1 | 12/2022 | Hill et al. |

FOREIGN PATENT DOCUMENTS

| | | | | |
|---|---|---|---|---|
| KR | 20170028622 | A | * | 3/2017 |
| KR | 101837897 | B1 | * | 3/2018 |
| WO | WO-2018101828 | A1 | * | 6/2018 ............... E02D 1/08 |

OTHER PUBLICATIONS

KR-101837897-B1, English Translation (Year: 2018).*
KR-20170028622-A, English Translation (Year: 2017).*
WO-2018101828-A1, English (Year: 2018).*
International Search Report and Written Opinion in related application PCT/US2022/070384 Apr. 7, 2022.
Foundation Performance Association Structural Committee, Guidelines for the Evaluation of Foundation Movement for Residential and Other Low Rise Buildings, Apr. 11, 2015.
Ronald Wyllys, University of Texas at Austin, Using Regression to Estimate and Predict, Jan. 15, 2003.
Sumitomo Forestry Co., Introducing a Precast Concrete Foundation Construction Method, Apr. 23, 2013.
International Search Report and Written Opinion for PCT/US2017/056217, dated Jan. 8, 2018.
International Search Report and Written Opinion for PCT/US2017/056207, dated Jan. 2, 2018.

* cited by examiner

METHODS AND APPARATUS FOR FOUNDATION MONITORING

CROSS-REFERENCE TO RELATED APPLICATIONS

This application claims benefit of U.S. provisional patent application Ser. No. 63/142,105, filed Jan. 27, 2021, and of U.S. provisional patent application Ser. No. 63/145,210, filed Feb. 3, 2021, which applications are herein incorporated by reference in their entireties.

BACKGROUND

Field

The present disclosure generally relates to a method for monitoring the elevation and movement of a foundation upon which a structure is built, and an apparatus for autonomous capture of the data required for foundation monitoring of both new and existing foundations.

Description of the Related Art

The earth is constantly changing and moving, and this has an impact on the structures that are built upon it. Unfortunately, around 17% of the foundations in certain US regions will experience foundation damage over their lifetime and the cost to repair foundation damage can vary significantly. If the damage is caught early, repair costs are substantially less than if the damage is identified later; the repair costs may be minimal with the timely implementation of just a change to a foundation maintenance program. If left undetected, or if ignored, foundation damage can render a structure uninhabitable.

Effective early detection of foundation problems may be facilitated by the acquisition of competent measurements of the foundation itself. For example, a sensor may be moved within a conduit in a foundation, and may take readings of hydrostatic head of a surrounding fluid at various locations in the foundation, each reading indicative of the elevation of the conduit—and thus the foundation—at each location. However, such techniques are cumbersome, and are subject to error due to temperature effects and physical phenomena such as gas breakout/dissolution in the surrounding fluid. Furthermore, measurements taken at lengthy time intervals may not reveal the true extent of foundation movement over time.

Thus, there is a need for improved processes that facilitate efficient, effective, and accurate monitoring of foundations and other structures.

SUMMARY

The present disclosure generally relates to systems, apparatus, and methods for the evaluation of foundations. In one embodiment, a foundation monitoring system includes a sensor cartridge assembly. The sensor cartridge assembly includes a first sensor disposed in a sensor tube and a sensor head attached to an end of the sensor tube. The sensor head contains a second sensor. The foundation monitoring system further includes a raceway configured for attachment to a foundation. The sensor tube is configured to be inserted into the raceway. The foundation monitoring system further includes a data transmitter configured to receive data from the first and second sensors, and convey the data to a controller.

In another embodiment, a sensor cartridge assembly for a foundation monitoring system includes a first sensor disposed in a sensor tube. A payout line is disposed in the sensor tube. The payout line couples the first sensor to an anchor point at a first end of the sensor tube and to a guide shoe at a second end of the sensor tube. The sensor cartridge assembly further includes a sensor head attached to the first end of the sensor tube.

In another embodiment, a method of monitoring a foundation, includes acquiring temperature and pressure data from first and second sensors installed within a sensor tube attached to the foundation. The method further includes determining the temperature and pressure data from the first and second sensors to be stabilized. The method further includes deriving, from the temperature and pressure data, a first elevation of the first sensor and a second elevation of the second sensor with respect to a predetermined datum.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, as the disclosure may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure concerns systems, apparatus, and methods for the evaluation of foundations. Such evaluation may be undertaken for one or more purpose, such as, without limitation, an assessment of suitability for occupancy, identification of maintenance needs, success of completed repairs, independent confirmation of construction quality, prediction of future foundation issues, confirmation of engineering calculations, rapid testing of foundation performance evaluation during real estate transactions, or the creation of an actuarial database for the purpose of creating an insurance product. Other purposes for such evaluation are also contemplated.

Embodiments of the present disclosure include the use of sensors deployed at one or more discrete locations. Each sensor is fixed in place at a corresponding discrete location. Embodiments of the present disclosure include the use of sensors that are smaller than conventional, currently used sensors, and thus present greater utility regarding location access and power usage. Embodiments of the present disclosure include the use of sensors that are substantially insulated from the effects of changing atmospheric conditions. Examples of such changing atmospheric conditions include intra-day and inter-day heating and cooling, such as direct and indirect heating from sunshine and cooling during periods of rain or darkness. A further example of such changing atmospheric conditions includes instant localized variations in atmospheric pressure due to wind.

Figure 1:
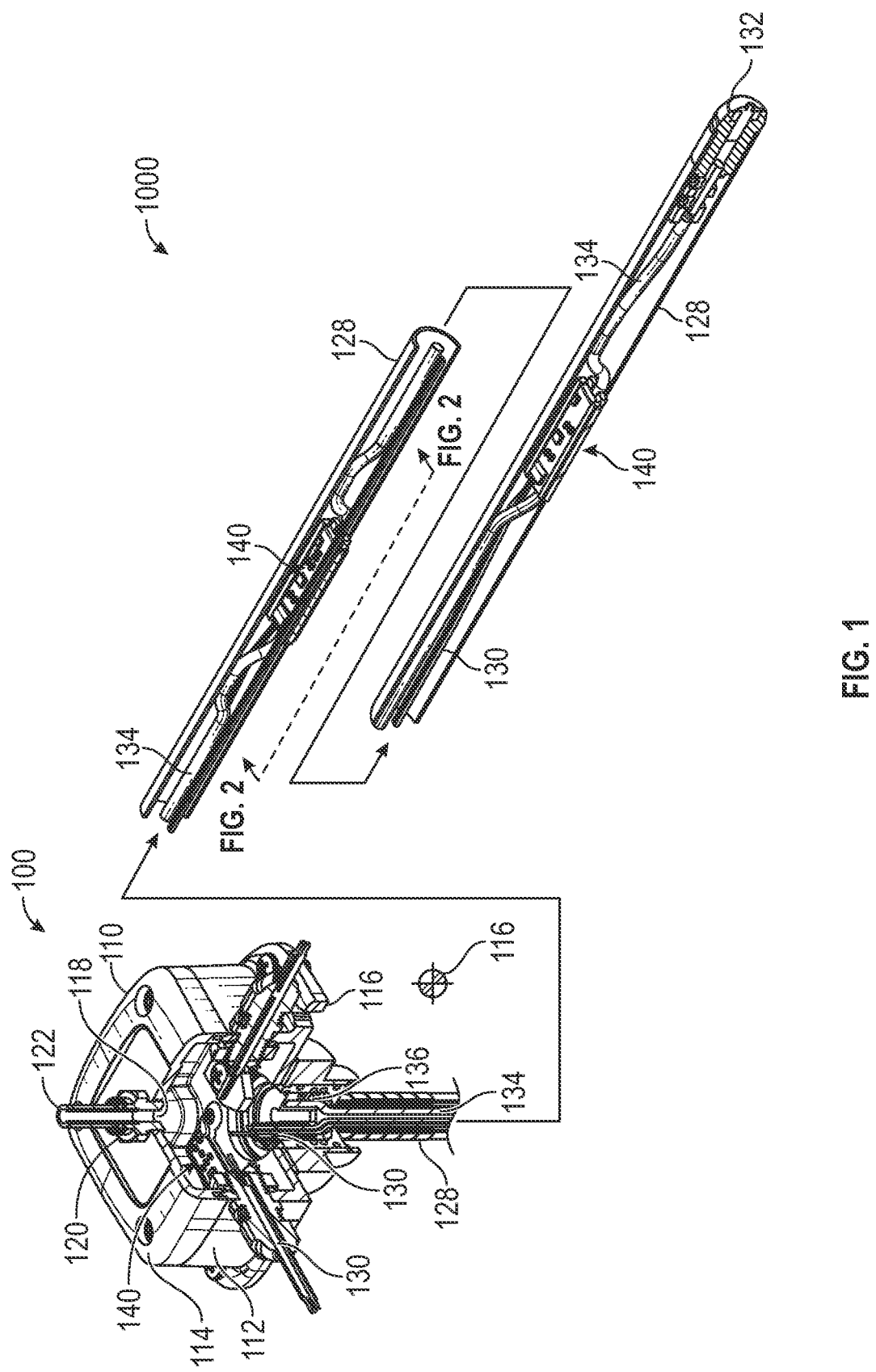
FIG. 1 is a combined isometric and cross-sectional view of components of a foundation monitoring system.

FIG. 1 is a combined isometric and cross-sectional view of components of a foundation monitoring system 1000. The foundation monitoring system 1000 includes a sensor cartridge assembly 100. Sensor cartridge assembly 100 includes a sensor head 110 coupled to a sensor tube 128. The sensor head 110 is a container including a body 112 and a lid 114. The sensor head 110 includes a datum 116 that is a reference point for measurements related to elevation of components, such as sensors, described below. The sensor head 110 includes a vent 118 that facilitates equalization of pressure between an interior and an exterior of the sensor head 110. As illustrated, the vent 118 is located in the lid 114 of the sensor head 110, however in some embodiments it is contemplated that the vent 118 may be positioned in the body 112 of the sensor head 110. A tubing adapter 120 at the vent 118 facilitates the coupling to the sensor head 110 of tubing or equipment, such as a pressure balance tube 122. The sensor head 110 contains a sensor 140 and associated wiring 130. In some embodiments, it is contemplated that the sensor 140 measures and transmits data representative of a fluid pressure, such as a hydrostatic pressure. In some embodiments, it is contemplated that the sensor 140 measures and transmits data representative of a temperature. In some embodiments, it is contemplated that the sensor 140 measures and transmits data representative of a temperature and a fluid pressure (such as a hydrostatic pressure).

As illustrated, a single sensor tube 128 is coupled to the sensor head 110. In some embodiments, it is contemplated that more than one sensor tube 128 may be coupled in parallel to the sensor head 110.

The sensor tube 128 contains one or more additional sensors 140 similar to sensor 140 in the sensor head 110, each additional sensor 140 coupled to associated wiring 130. In some embodiments, it is contemplated that the sensors 140 within the sensor tube 128 are spaced at regular intervals along the sensor tube 128. For example, each sensor 140 may be spaced ten feet (3 m) apart. Additionally, or alternatively, some sensors 140 may be spaced closer together along the sensor tube 128, and other sensors 140 may be spaced further apart along the sensor tube 128. For example, two sensors, A and B, may be spaced five feet (1.5 m) apart and a third sensor, C, may be spaced ten feet (3 m) from sensor B. Furthermore, in some embodiments, it is contemplated that each sensor 140 is positioned within the sensor tube 128 such that the location of each sensor 140 along the sensor tube 128 from a reference point (such as the datum 116) is known with reasonable accuracy, such as to within three inches (7.6 cm), to within two inches (5.1 cm), to within one inch (2.5 cm), to within half an inch (1.3 cm), or to within a quarter of an inch (0.6 cm).

As illustrated, in some embodiments, it is contemplated that each sensor 140 within the sensor tube 128 is connected to wiring 130 that is routed within the sensor tube 128 from each sensor 140 to the sensor head 110. In some embodiments, it is contemplated that the wiring 130 connected to each corresponding sensor 140 may be discrete from other wiring 130 connected to another sensor 140. In some embodiments, it is contemplated that each sensor 140 may be connected to common wiring 130. In some embodiments, it is contemplated that the wiring 130 for individual sensors 140 may be bundled together as an integrated unit. In an example, wiring 130 connected to a first sensor 140 may be attached to wiring 130 connected to a second sensor 140 by one or more clips, cable ties, encapsulations, or sheaths.

The wiring 130 conveys electrical power to each sensor 140 and/or facilitates telemetry of data from each sensor 140 to the sensor head 110. In some embodiments, it is contemplated that one or more sensor 140 may be powered by a battery instead of, or in addition to, being powered via the wiring 130. In some embodiments, it is contemplated that data from one or more sensor 140 may be telemetered wirelessly. In some embodiments, it is contemplated that the wiring 130 may include an optical fiber line for the telemetry of data from one or more sensor 140. In some embodiments, it is contemplated that command signals may be sent to one or more sensor 140 via the wiring 130 and/or wirelessly.

A guide shoe 132 is located at an end of the sensor tube 128. In some embodiments, it is contemplated that an exterior surface of the guide shoe 132 may be rounded or chamfered. In some embodiments, it is contemplated that the guide shoe 132 is vented to permit fluids to enter the sensor tube 128 but not exit the sensor tube 128. In some embodiments, it is contemplated that the guide shoe 132 is vented to permit fluids to exit the sensor tube 128 but not enter the sensor tube 128. In some embodiments, it is contemplated that the guide shoe 132 is vented to permit fluids to enter and exit the sensor tube 128. In some embodiments, it is contemplated that the guide shoe 132 is not vented, thereby preventing entry of fluids into, and exit of fluids from, the sensor tube 128.

A payout line 134 within the sensor tube 128 is coupled to the guide shoe. The payout line 134 is coupled to each sensor 140 within the sensor tube 128 and to an anchor point 136. As illustrated, the anchor point 136 is situated at or near to the location where the sensor tube 128 is coupled to the sensor head 110. In some embodiments, it is contemplated that the anchor point 136 may be situated at other locations, such as elsewhere within the sensor head 110.

The payout line 134 facilitates the placement of each sensor 140 within the sensor tube 128 at predetermined locations and separation distances, as described above.

When the foundation monitoring system 1000 is deployed at a foundation and/or structure to be monitored, an identification of the location of each sensor 140 within the sensor tube 128 with respect to the foundation/structure is facilitated by the use of the payout line 134 to place each sensor 140 within the sensor tube 128. In some embodiments, it is contemplated that when deployed, the location of each sensor 140 within the sensor tube 128 with respect to the foundation/structure is correlated against a known reference point of the foundation/structure. For example, such a correlation may be achieved via photographs, a verification of a construction plan, or otherwise as known by one skilled in the art of geospatial location.

In some embodiments, it is contemplated that the payout line 134 may be a wire or rod that is sufficiently stiff to withstand an axial compression load associated with being pushed into the sensor tube 128, yet sufficiently flexible to conform to curvatures encountered during deployment of the sensor tube 128 at the foundation/structure. In an example, the payout line 134 is a high tensile strength wire, such as a wire used for electric fences. In some embodiments, it is contemplated that the payout line 134 may be corrosion-resistant. In some embodiments, it is contemplated that the payout line 134 may be readily wetted to a fluid introduced into the sensor tube 128.

In some embodiments, it is contemplated that the wiring 130 and the payout line 134 may be bundled together as an integrated unit. In an example, the wiring 130 may be attached to the payout line 134 by one or more clips, cable ties, encapsulations, or sheaths.

In some embodiments, it is contemplated that the wiring 130 or the payout line 134 may be adapted to perform the functions of both the wiring 130 and the payout line 134. In an example, wiring 130 is electrically or optically coupled to one or more sensor 140, and facilitates the placement of each sensor 140 within the sensor tube 128 at predetermined locations and separation distances, as described above. In another example, the payout line 134 is coupled to one or more sensor 140 within the sensor tube 128, and conveys electrical power to each sensor 140 and/or facilitates telemetry of data from each sensor 140 to the sensor head 110.

The payout line 134 mechanically couples each sensor 140 within the sensor tube 128 to restrict relative horizontal movement between each sensor 140 within the sensor tube 128 over time, such as due to thermal expansion or contraction of the payout line 134 and/or the wiring 130. Thus, when the sensor tube 128 is deployed at a foundation/structure, the data obtained over time from each sensor 140 within the sensor tube 128 is readily correlated with a corresponding single specific location of the foundation/structure, thereby facilitating an accurate assessment of the foundation/structure over time.

Figure 2:
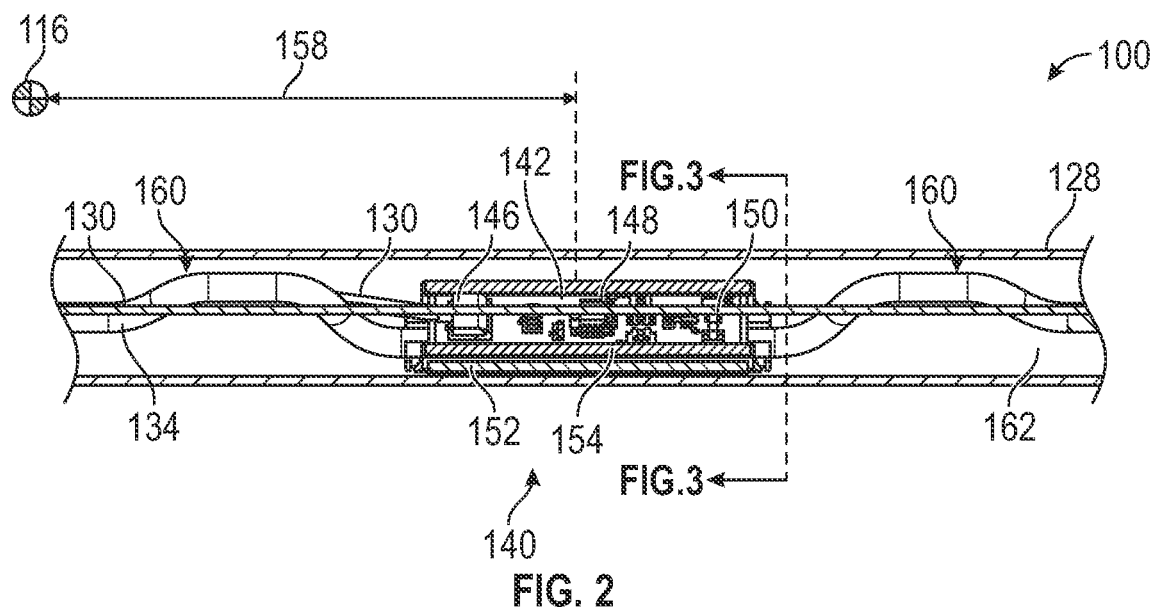
FIG. 2 is a combined elevation and cross-sectional view of selected components of the foundation monitoring system of FIG. 1.
Figure 3:
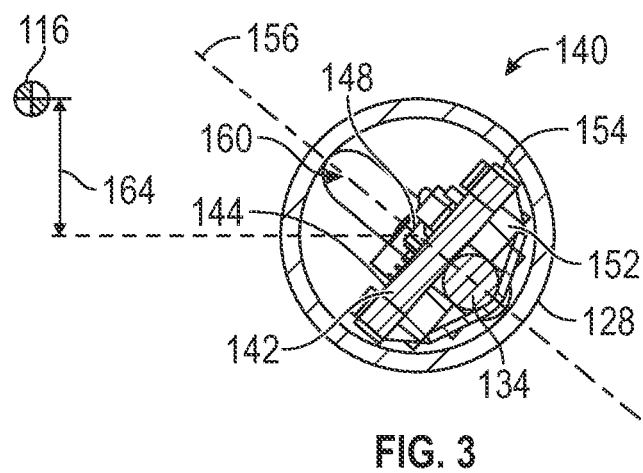
FIG. 3 is a cross-sectional view of a portion of the apparatus of FIG. 2.

FIG. 2 is a combined elevation and cross-sectional view of selected components of the foundation monitoring system 1000 of FIG. 1. FIG. 3 is a cross-sectional view of a portion of the sensor cartridge assembly 100 of FIG. 2.

Referring to both FIGS. 2 and 3, sensor 140 disposed in sensor tube 128 is representative of any sensor 140 of the foundation monitoring system 1000. In some embodiments, as illustrated, it is contemplated that sensor 140 includes a printed circuit board 142 with a surface 144 on which are attached a connector 146 for attaching to wiring 130, one or more sensor chip 148, and a communication chip 150. As described above, the one or more sensor chip 148 is configured to measure a pressure and/or a temperature of the ambient environment at the sensor 140. In some embodiments, it is contemplated that the sensor 140 may include additional circuitry (such as an additional chip, an accelerometer, or the like) for measuring additional parameters, such as motion, vibration, time, etc. In some embodiments, it is contemplated that the sensor 140 and/or the one or more sensor chip 148 itself may include a memory.

The communication chip 150 is configured to transmit data measured by the one or more sensor chip 148 and any additional circuitry. The communication chip 150 transmits such data via the connector 146 and associated wiring 130. Additionally, or alternatively, in some embodiments it is contemplated that the communication chip 150 may transmit at least a portion of such data wirelessly.

FIG. 2 further depicts a payout distance 158 of the sensor 140 with respect to a known reference point, such as datum 116. As illustrated, the payout distance 158 is representative of the distance along the sensor tube 128 of the sensor chip 148 of sensor 140 from the datum 116. The payout distance 158 thus refers to the location of the sensor 140 along the sensor tube 128.

As illustrated, in some embodiments it is contemplated that a portion 160 of the payout line 134 near to the sensor 140 may be contorted into a "u" shape, or the like. As shown in FIG. 3, the sensor 140 is attached to the payout line 134 by a centralizer 152 and a retainer 154 such that the contorted portion 160 of the payout line 134 is oriented along an axis 156 that is substantially perpendicular to the surface 144 of the printed circuit board 142 of the sensor 140. In an example, the axis 156 is 85 to 90 degrees, such as 86 to 90 degrees, or 88 to 90 degrees from the surface 144 of the printed circuit board 142. The contorted portion 160 of the payout line 134 enables the payout line 134 to transfer an axial force to the sensor 140 along the sensor tube 128.

Additionally, the centralizer 152 facilitates the placement of the sensor chip 148 substantially at the radial center of the sensor tube 128, such as within a half inch (1.3 cm), within a quarter inch (0.6 cm), or within an eighth of an inch (0.3 cm) of the radial center of the sensor tube 128. In some embodiments, it is contemplated that the contorted portion 160 of the payout line 134 bears against one portion of a sidewall of the sensor tube 128 and the centralizer 152 and/or retainer 154 bear(s) against one or more other portions of the sidewall of the sensor tube 128 in order to facilitate placement of the sensor chip 148 at or near to the radial center of the sensor tube 128. In some embodiments, the contorted portion 160 of the payout line 134, the centralizer 152 and/or the retainer 154 maintain placement of the sensor chip 148 at or near to the radial center of the sensor tube 128 regardless of the rotational orientation of the printed circuit board 142 within the sensor tube 128.

In some embodiments, it is contemplated that the contorted portion 160 of the payout line 134 may be omitted, such that the centralizer 152 and/or retainer 154 alone maintain placement of the sensor chip 148 at or near to the radial center of the sensor tube 128. In some embodiments, it is contemplated that the centralizer 152 may be omitted. In such embodiments, the retainer 154 attaches the payout line 134 to the printed circuit board 142. Additionally, the retainer 154/printed circuit board 142 may be self-centralizing.

In some embodiments, it is contemplated that the sensor 140 may be configured such that the sensor chip 148 is not placed at or near the radial center of the sensor tube 128. For example, the sensor 140 may include an attachment and/or retainer 154 configured to offset the sensor chip 148 from the radial center of the sensor tube 128. Such an example may include the use of a weight attached to the sensor so that the rotational orientation of the sensor 140 is maintained relatively constant by the Earth's gravity. Alternatively, a biasing element, such as a bow spring, may be attached to the sensor 140 in order to force the sensor 140 against the sidewall of the sensor tube 128, thereby holding the sensor 140 rotationally in place.

In another example, the sensor 140 may be configured such that the sensor chip 148 may be positioned in a zone that includes the radial center of the sensor tube 128 and includes a region surrounding the radial center of the sensor tube 128.

In embodiments in which a sensor chip 148 of a sensor 140 is positioned at the radial center of a sensor tube 128, it is contemplated that the elevation of the point of measurement of the sensor chip 148 remains at the radial center of the sensor tube 128, and hence at the same elevation with respect to the sensor tube 128, even if the sensor 140 is rotated within the sensor tube 128. Therefore, even if the sensor 140 is rotated within the sensor tube 128, such as during an interval between acquiring measurements from the sensor 140, each measurement is indicative of the elevation of the sensor tube 128 itself with respect to the corresponding sensor head 110. Thus, in comparing measurements taken at different times, a change in the magnitude of the data values obtained from the sensor 140 can indicate that there has occurred a change in the elevation of the sensor tube 128, and hence a change in the elevation of the portion of the foundation to which the sensor tube 128 is attached.

In embodiments in which a sensor chip 148 of a sensor 140 is positioned near to the radial center of a sensor tube 128, it is contemplated that should the sensor 140 become rotated within the sensor tube 128 between or during acquiring measurements, any error in later measurements due to a change in elevation of the point of measurement of the sensor chip 148 with respect to the sensor tube 128 may be minor compared to other sources of inaccuracy, such as density variations of the sensor fluid 162 (described below) within the sensor tube 128.

Nevertheless, it is contemplated that the propensity is low for a sensor 140 to become rotated within a sensor tube 128 between or during acquiring measurements, after the sensor tube 128 has been installed at work location. Hence, the propensity is low for a change in elevation with respect to the sensor tube 128 of the point of measurement of the sensor chip 148. Therefore, in embodiments in which a sensor chip 148 of a sensor 140 is positioned away from the radial center of a sensor tube 128, it is contemplated that rotation of the sensor 140 between or during acquiring measurements would not be a root cause of error when comparing the measurements.

The sensor tube 128 contains a sensor fluid 162, such as a single phase fluid. In some embodiments, the sensor fluid 162 is a dielectric fluid, such as distilled water. Alternatively, the sensor fluid 162 may be a dielectric fluid with natural low water absorption propensity, such as is commonly used in liquid filled transformers. In other embodiments, the sensor fluid 162 is a dielectric fluid such as is common in electric discharge machining. Such fluids are suitable for exposure to air in their natural use condition, and are approved for use around personnel. In other embodiments, the sensor fluid 162 is a synthetic dielectric fluid. In other embodiments, the sensor fluid 162 is a dielectric oil, such as a mineral oil. Selection of a sensor fluid 162 can depend upon such aspects as local temperature extremes, environmental considerations, local regulations, etc. The sensor fluid 162 fills the sensor tube 128 such that each sensor 140 within the sensor tube 128 is immersed in the sensor fluid 162.

FIG. 3 further depicts an elevation 164 of the sensor 140 with respect to a known reference point, such as datum 116. In some embodiments, it is contemplated that the elevation 164 is derived from a measurement of hydrostatic pressure of the sensor fluid 162 by the sensor chip 148. The hydrostatic pressure of the sensor fluid 162 is a function of the density of the sensor fluid 162. The density of the sensor fluid 162 is a function of the temperature of the sensor fluid 162. Measurements of temperature and pressure by the sensor chip 148 of each sensor 140 thus provide data from which the elevation 164 of each sensor 140 is derived. The elevation 164 is recorded for each sensor 140 corresponding to measurements obtained from each sensor 140 over time.

During assembly of the sensor cartridge assembly 100, the sensor tube 128 is filled with sensor fluid 162. In some embodiments, it is contemplated that the sensor tube 128 is filled with sensor fluid 162 in a manner that removes air from the sensor tube 128. For example, the sensor fluid 162 may be introduced into the sensor tube 128 via a capillary line. In another example, the sensor tube 128 is positioned at an incline to promote the escape of air during filling with sensor fluid 162. Additionally, or alternatively, a vacuum may be applied to the sensor tube 128 to evacuate air while filling the sensor tube 128 with sensor fluid 162. Furthermore, the sensor tube 128 may be vibrated during and/or after introduction of the sensor fluid 162 in order to dislodge air bubbles so that the air bubbles can escape from the sensor tube 128.

Figure 4:
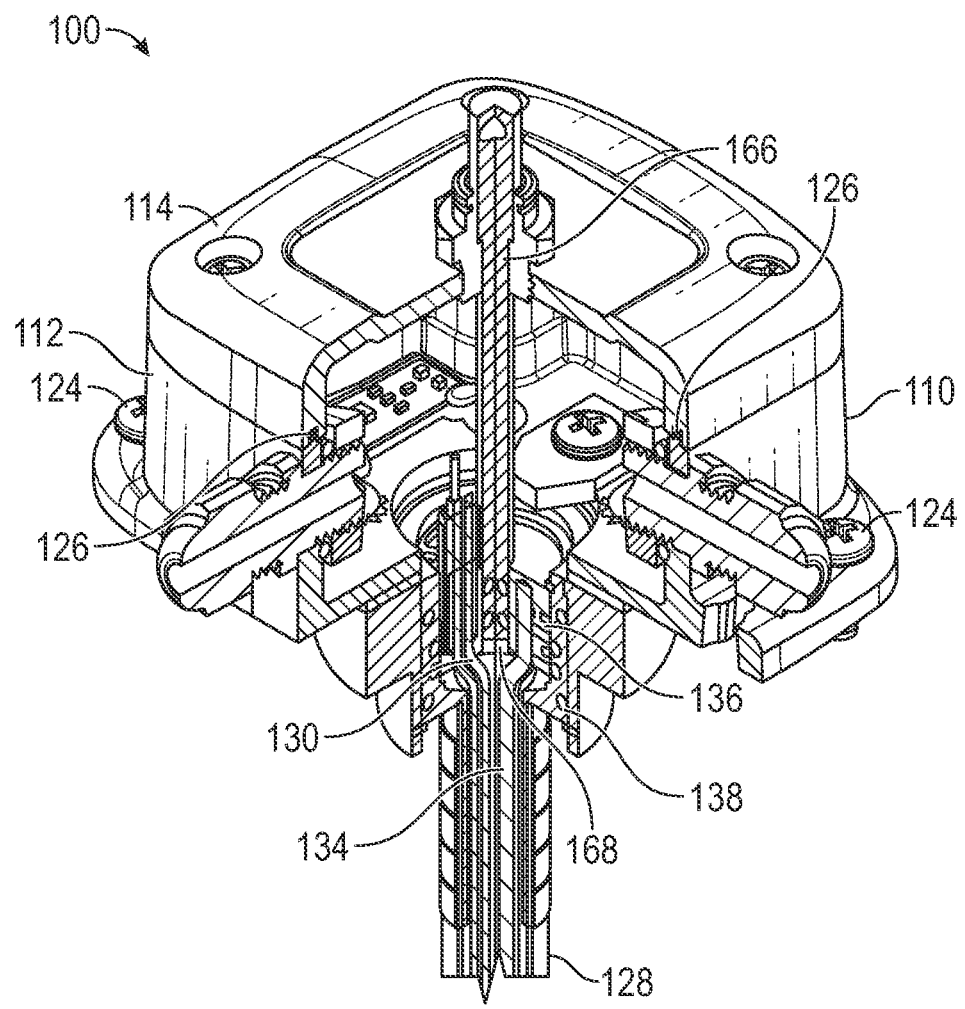
FIG. 4 is a detailed view of a portion of FIG. 1.
Figure 5:
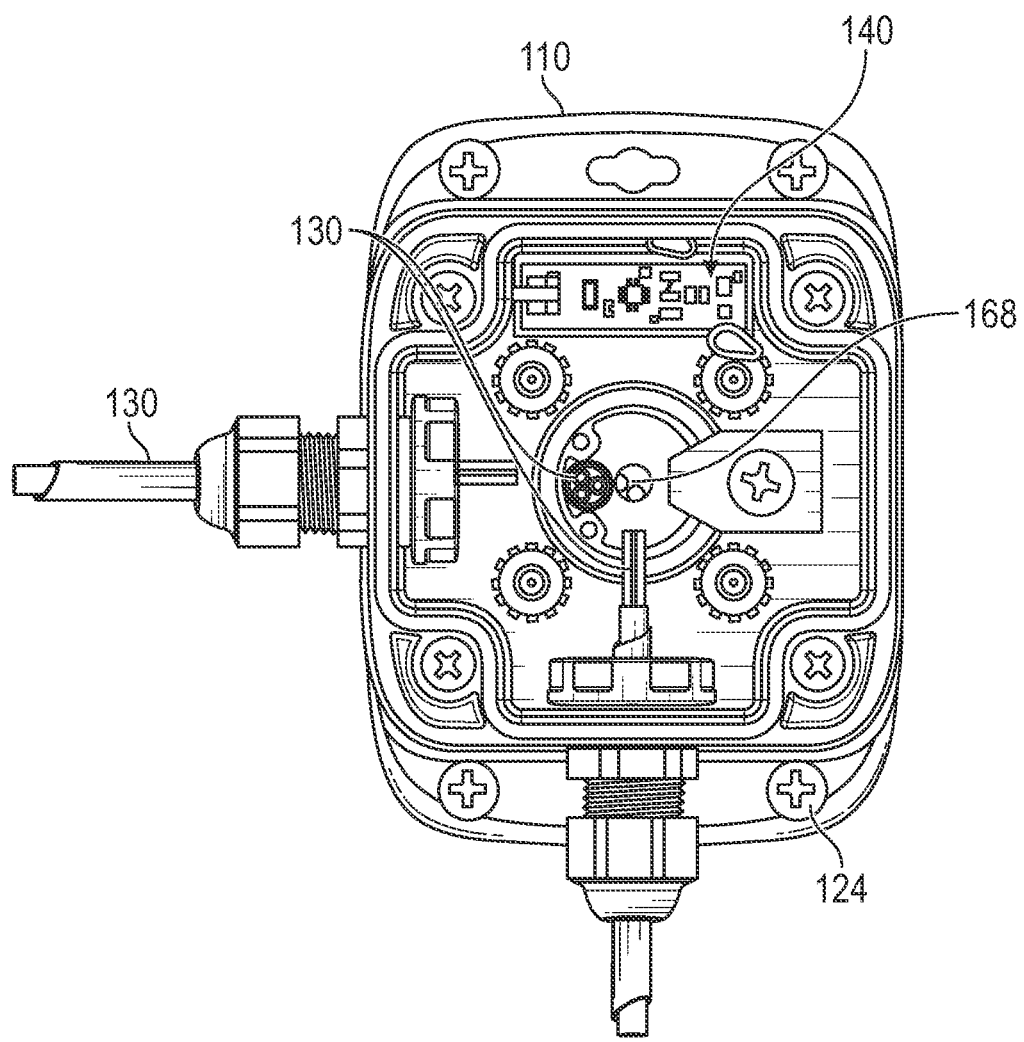
FIG. 5 is a section view in a plan orientation of the components depicted in FIG. 4.

FIG. 4 is a detailed view of a portion of FIG. 1, and FIG. 5 is a section view in a plan orientation of the components depicted in FIG. 4. A seal 126 prevents ingress of foreign material and water between component parts of the sensor head 110, such as the lid 114 and the body 112. One or more mounting fastener 124 facilitates the attachment of the sensor head 110 to a suitable mounting platform, such as a sensor head base described below. The sensor head 110 is attached to sensor tube 128 before installation of the sensor cartridge assembly 100 at a desired location at a foundation or building.

A swivel 138 at the anchor point 136 allows the sensor head 110 to be rotated with respect to the sensor tube 128 and the payout line 134. In some embodiments, it is contemplated that the swivel 138 may be omitted. A seal stem 166 inserted into a fluid port 168 of the swivel 138 (or into the sensor tube 128 itself) isolates the sensor fluid 162 in the sensor tube 128 from other fluid in the sensor head 110. The seal stem 166 mitigates potential loss of sensor fluid 162 from the sensor cartridge assembly 100 from spillage during transport and installation of the sensor cartridge assembly 100. Once the sensor tube 128 has been installed at a desired location at a foundation or building, the seal stem 166 is removed from the swivel 138. In an alternative embodiment, a valve or a rupture disc is disposed at the swivel 138 in place of the seal stem 166. Upon removal of the seal stem 166 from the swivel 138, the fluid port 168 is open such that a pressure within the sensor head 110 is communicated to the sensor fluid 162 in the sensor tube 128.

The anchor point 136 for the payout line 134 is at the swivel 138, and the wiring 130 from the sensor tube 128 is routed through the swivel 138. In some embodiments, it is contemplated that the wiring 130 from the sensor tube 128 is routed through a sealed penetration through the swivel. In some embodiments, it is contemplated that the wiring 130 may terminate at an electrical connector within or outside the sensor head 110 to facilitate connection to additional wiring 130 routed to other components of the foundation monitoring system 1000, such as another sensor head 110, a power supply, and/or a controller. In such embodiments, it is contemplated that the electrical connector is suitable for use in a wet environment.

The swivel 138 permits relative rotation between the sensor head 110 and the sensor tube 128. In some embodiments, it is contemplated that the swivel 138 includes a design incorporating a slip ring.

Figure 6:
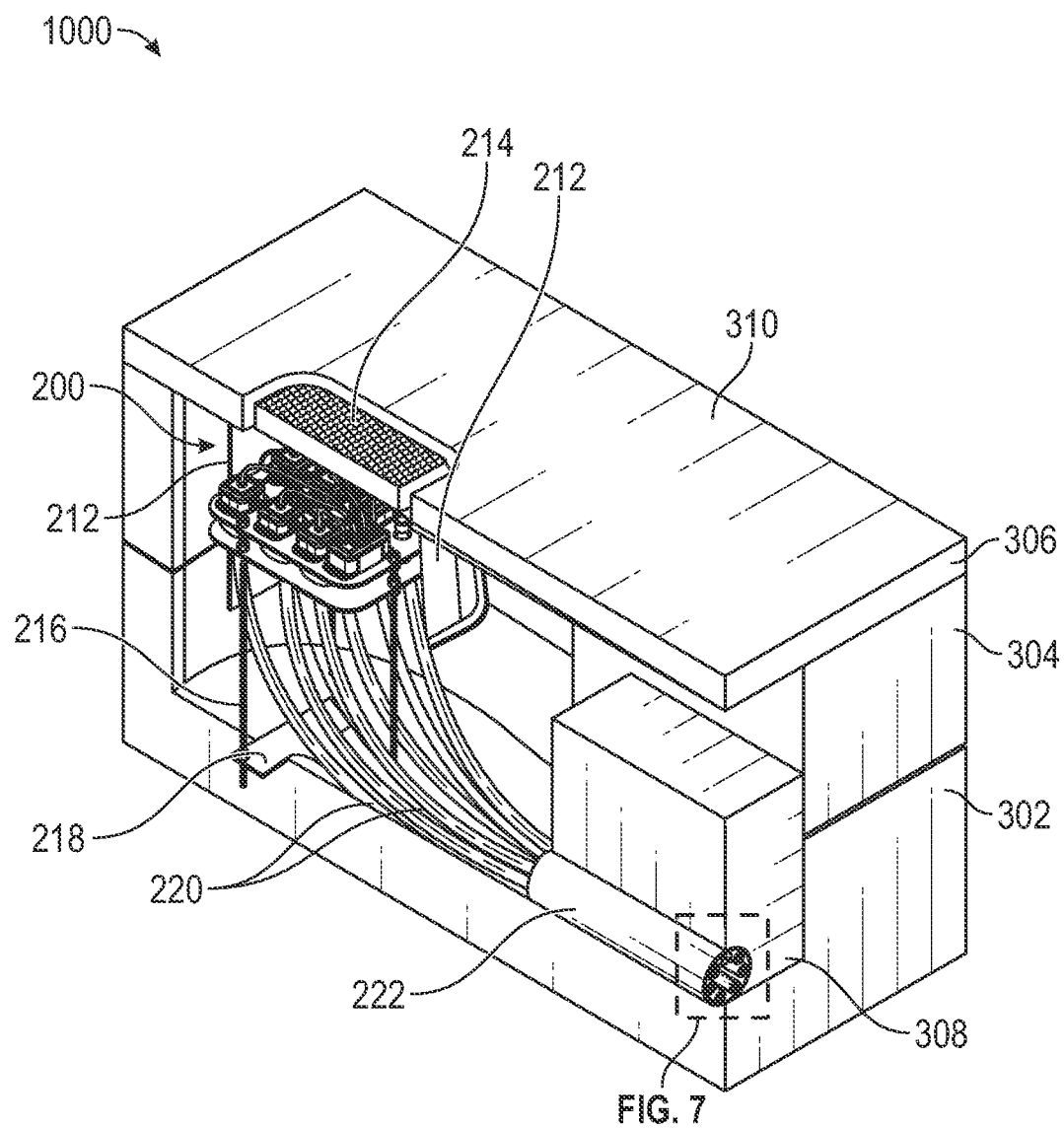
FIG. 6 is a combined isometric and cross-sectional view of components of a foundation monitoring system in an exemplary installation.

FIG. 6 is a combined isometric and cross-sectional view of components of the foundation monitoring system 1000 in an exemplary installation. Depicted are the typical soil layers found near a building foundation. For example, where a site initially is developed for construction, there exists a layer of native soil 302 with particular geotechnical properties. Often, a site is prepared first by a developer that brings in imported soil 304 to place on top of the native soil 302. Imported soil 304 is placed for a variety of reasons, including the compensation of native soil 302 geotechnical properties, an adjustment to the site elevation, a modification to the drainage plan, etc. Topsoil 306 is usually placed on top of the soils surrounding the construction site.

A sensor head assembly 200 that includes one or more sensor heads 110 is located in a container 212, such as a utility box, that is located below ground level 310. Each sensor head 110 is part of a discrete sensor cartridge assembly 100. In some embodiments, it is contemplated that the container 212 is fitted with a cover 214, which, in the illustrated example, is at ground level 310. In some of such embodiments, it is contemplated that the cover 214 may be thermally insulated. In some embodiments, the cover 214 may be omitted. In some embodiments, it is contemplated that at least a portion of the container 212 may be above ground level 310.

The sensor head assembly 200 is affixed to an anchor base 218 via connectors 216. In some embodiments, it is contemplated that the anchor base 218 is set in concrete. In some embodiments, it is contemplated that the anchor base 218 is set in a soil, such as native soil 302, imported soil 304, or backfill soil 308.

A tubular conduit, such as raceway 220, extends below each corresponding sensor head 110 below ground level 310, such as through concrete, through the native soil 302, through the imported soil 304, and/or through backfill soil 308. The sensor tube 128 of each sensor cartridge assembly 100 extends within a corresponding raceway 220. As illustrated, a plurality of raceways 220 are routed through a raceway protector 222. The raceway protector 222 is shown as being deployed in backfill soil 308. In some embodiments, it is contemplated that the raceway protector 222 may be deployed in concrete. Sensors 140 within an individual sensor tube 128 are afforded at least some protection from external elements by being situated within the sensor tube 128, which is within a raceway 220, which is within the raceway protector 222, which is within backfill soil 308 and/or concrete. Moreover, placing the sensor head assembly 100 below ground level 310 allows the sensor fluid 162 inside each sensor cartridge assembly 100, raceway 220, and sensor tube 128 to benefit from the thermal insulating properties of the topsoil 306, imported soil 304, backfill soil 308, and (depending on the depth) the native soil 302 at the construction site.

In some embodiments, it is contemplated that a drain is included to route water out of the container 212. In an example, the drain includes a hole or excavation backfilled with sand or gravel.

Figure 7:
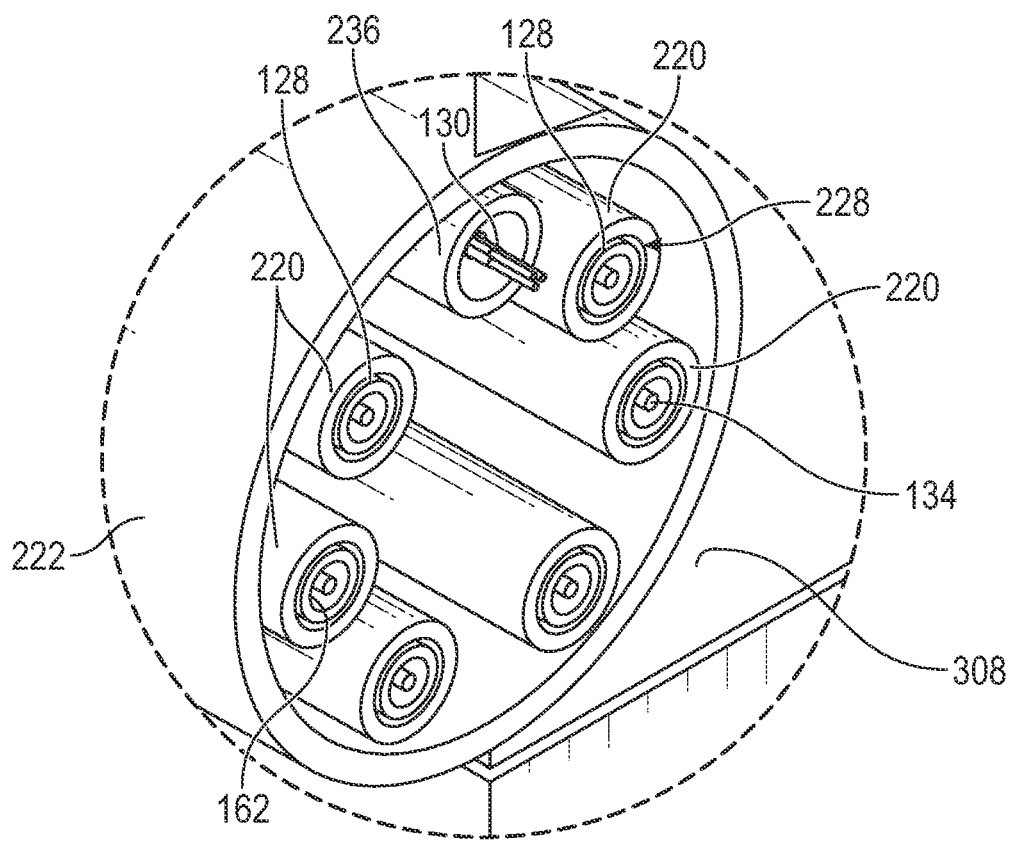
FIG. 7 is a detailed view of a portion of FIG. 6.

FIG. 7 is a detailed view of a portion of FIG. 6. The raceway protector 222 is illustrated as containing a plurality of raceways 220 and an electrical raceway 236. Each raceway 220 contains a sensor tube 128 of a corresponding sensor cartridge assembly 100. The wiring 130 in the electrical raceway 236 (at the 12 o'clock position) is routed between the sensor head assembly 200 and a power supply, and/or a controller. In each of the raceways 220, a sensor tube 128, payout line 134, and sensor fluid 162 are depicted; wiring 130 has been omitted for clarity. An annulus 228 exists between each raceway 220 and the corresponding sensor tube 128. In some embodiments, it is contemplated that the annulus 228 contains a fluid, such as sensor fluid 162.

Figure 8:
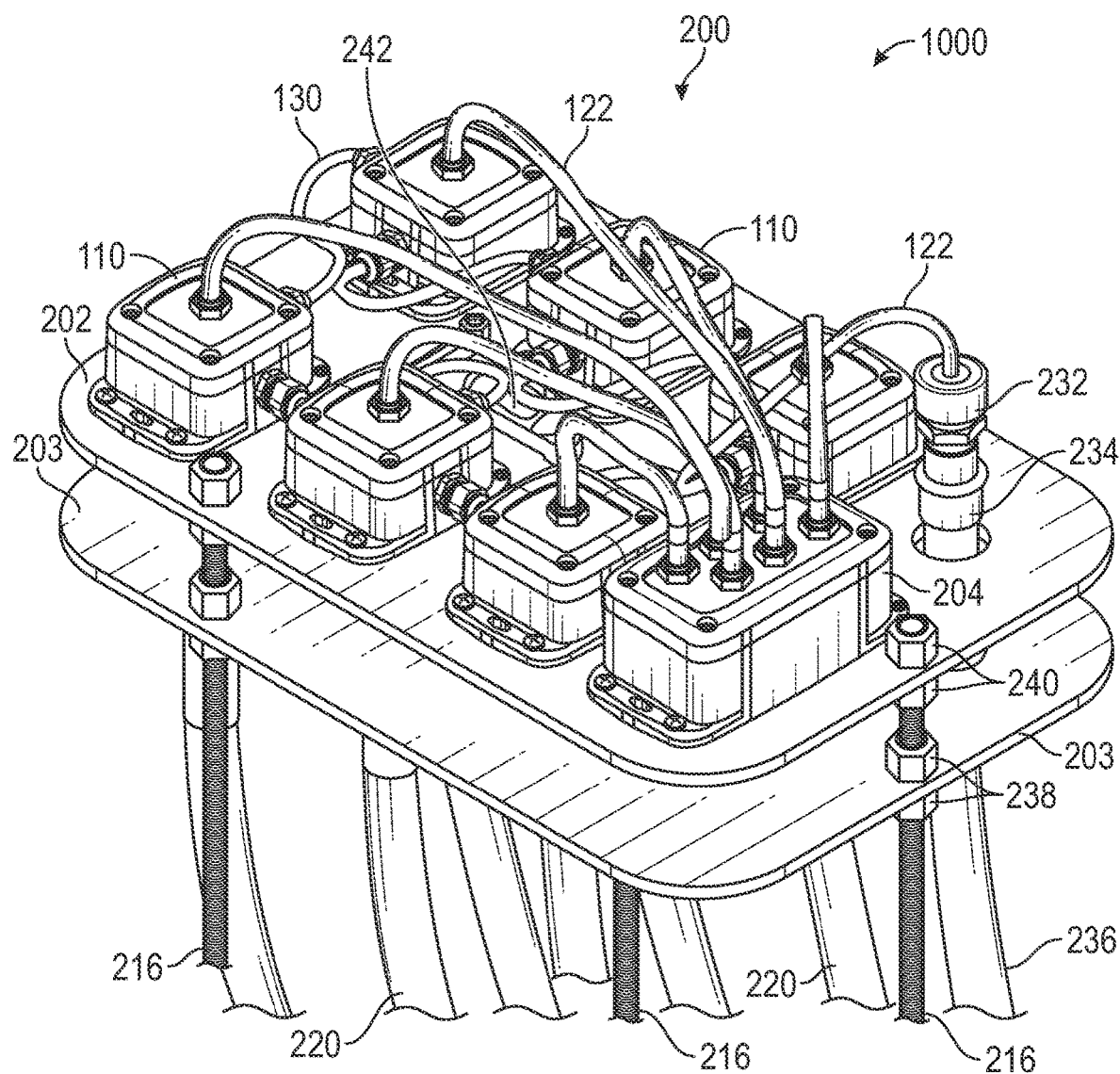
FIG. 8 is an isometric view of a sensor head assembly of a foundation monitoring system.

FIG. 8 is an isometric view of components of sensor head assembly 200 of foundation monitoring system 1000. The sensor head assembly 200 is illustrated as including a plurality of sensor heads 110. In some embodiments, it is contemplated that the sensor head assembly 200 may include a single sensor head 110. In an example, a plurality of sensor cartridge assemblies 100, and hence a plurality of sensor heads 110, could be required if the foundation being measured has a relatively large surface area (such as about 2,500 square feet (about 232 square meters) or greater), or if readings are required from within the foundation in addition to perimeter readings.

Each sensor head 110 is mounted on a sensor head base 202. The pressure balance tube 122 from each sensor head 110 is coupled to a pressure balance chamber 204 that is also mounted on the sensor head base 202. As shown, each pressure balance tube 122 is coupled to the pressure balance chamber 204 in parallel. In some embodiments, it is contemplated that the pressure balance tubes 122 of at least two sensor heads 110 may be coupled in series with the pressure balance chamber 204.

Each pressure balance tube 122 is looped from the top of a corresponding sensor head 110 to the top of the pressure balance chamber 204. Each loop is oriented upwards from the top of the corresponding sensor head 110 then downwards to the top of the pressure balance chamber 204. Such an arrangement is beneficial in the event of flooding, such that rising water is inhibited from entering the sensor head 110. The ability of the sensor cartridge assembly 100 to remain submersed and still acquire sensor data has particular utility in establishing early indications of foundation damage during events like floods and hurricanes.

In some embodiments, not shown, it is contemplated that each sensor head 110 may be coupled to a corresponding individual pressure balance chamber instead of a common pressure balance chamber 204. In such embodiments, it is contemplated that each individual pressure balance chamber is connected to the corresponding sensor head 110 at the tubing adapter 120 of the sensor head 110. It is further contemplated that each individual pressure balance chamber may include a bladder filled with air or with nitrogen, such as pure nitrogen at 95% or greater purity. It is further contemplated that the bladder may be pressurized, such that the contents are released into the sensor head 110 upon opening a valve between the sensor head 110 and the individual pressure balance chamber.

Returning to FIG. 8, wiring 130 external to the sensor head 110 can be routed as needed. As illustrated, in an exemplary installation, wiring 130 is routed from a sensor head 110 through a cord grip 232 and a conduit adapter 234 into an electrical raceway 236. Such an installation is waterproof. It is contemplated that the electrical raceway 236 routes the wiring 130 to a power source and/or control unit, such as a data transmitter as described below.

The sensor head assembly 200 includes an assembly base 203 below the sensor head base 202. The assembly base 203 is coupled to a threaded portion of each connector 216 from the anchor base 218 by one or more fasteners 238, such as nuts. The sensor head base 202 is also coupled to the threaded portion of each connector 216 from the anchor base 218 by one or more fasteners 240, such as nuts. As illustrated, in some embodiments it is contemplated that the sensor head assembly 200 includes a levelling indicator 242. The levelling indicator 242 provides a reference showing whether or not the sensor head base 202 is oriented horizontally. Modification of the orientation of the sensor head base 202 with respect to horizontal is achieved by adjusting the fasteners 240 with respect to one or more connector 216.

In some embodiments, it is contemplated that data from a sensor 140 within each of three (or more) sensor heads 110 mounted on the sensor head base 202 may be used to indicate whether or not the sensor head base 202 is horizontal.

In some embodiments, it is contemplated that the sensor head base 202 may be substantially horizontal, such as within ten degrees, within five degrees, within three degrees, or within one degree of horizontal. In some embodiments, it is contemplated that the sensor head base 202 may not be substantially horizontal, for example, where only a single sensor head 110 is installed on the sensor head base 202. Nevertheless, maintaining the sensor head base 202 substantially horizontal facilitates appropriate positioning of the pressure balance chamber 204 to provide for pressure balancing between each sensor head 110, and to mitigate a risk of flood water ingress into a sensor head 110.

Figure 9:
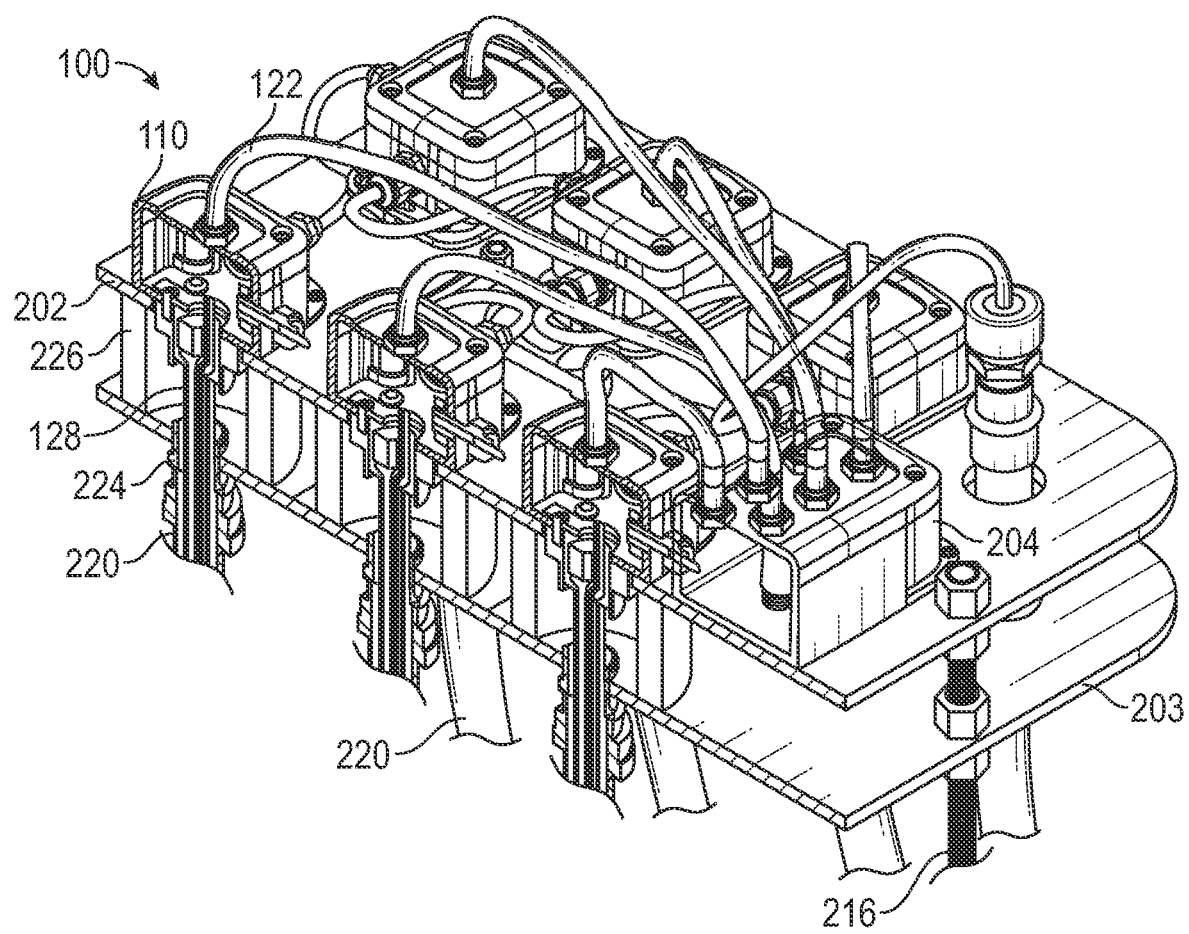
FIG. 9 is a combined isometric and cross-sectional view of the components depicted in FIG. 8.

FIG. 9 is a combined isometric and cross-sectional view of the components depicted in FIG. 8. Each raceway 220 is connected to the assembly base 203 via a corresponding raceway adapter 224. The sensor tube 128 of each sensor cartridge assembly 100 extends from each corresponding sensor head 110 and through a corresponding raceway adapter 224 into the corresponding raceway 220. Each sensor tube 128 extends between the sensor head base 202 and the assembly base 203, and is surrounded by a corresponding boot 226 that is coupled to the sensor head base 202 and to the assembly base 203. Each boot 226 inhibits the entry of debris or other foreign matter into each raceway 220.

In some embodiments, it is contemplated that each boot 226 is sufficiently flexible to allow for adjustment of the sensor head base 202 when positioning the sensor head base 202 substantially horizontal, while maintaining contact with the sensor head base 202 and with the assembly base 203. In an example, the boot 226 is made of an elastomer. In some embodiments, it is contemplated that each boot 226 may seal against the sensor head base 202. In some embodiments, it is contemplated that each boot 226 may seal against the assembly base 203.

In some embodiments, it is contemplated that a single boot 226 may surround a single sensor tube 128. In some embodiments, it is contemplated that a single boot 226 may surround a plurality of sensor tubes 128.

In some embodiments, it is contemplated that the assembly base 203 and the boot 226 may be omitted. In such embodiments, the sensor head 110 may be coupled to the sensor tube 128 and to the corresponding raceway 220 by a bushing. In an example, the bushing includes a top connection to the sensor head 110, an outer bottom connection to the raceway 220, and an inner bottom connection to the sensor tube 128.

Figure 10:
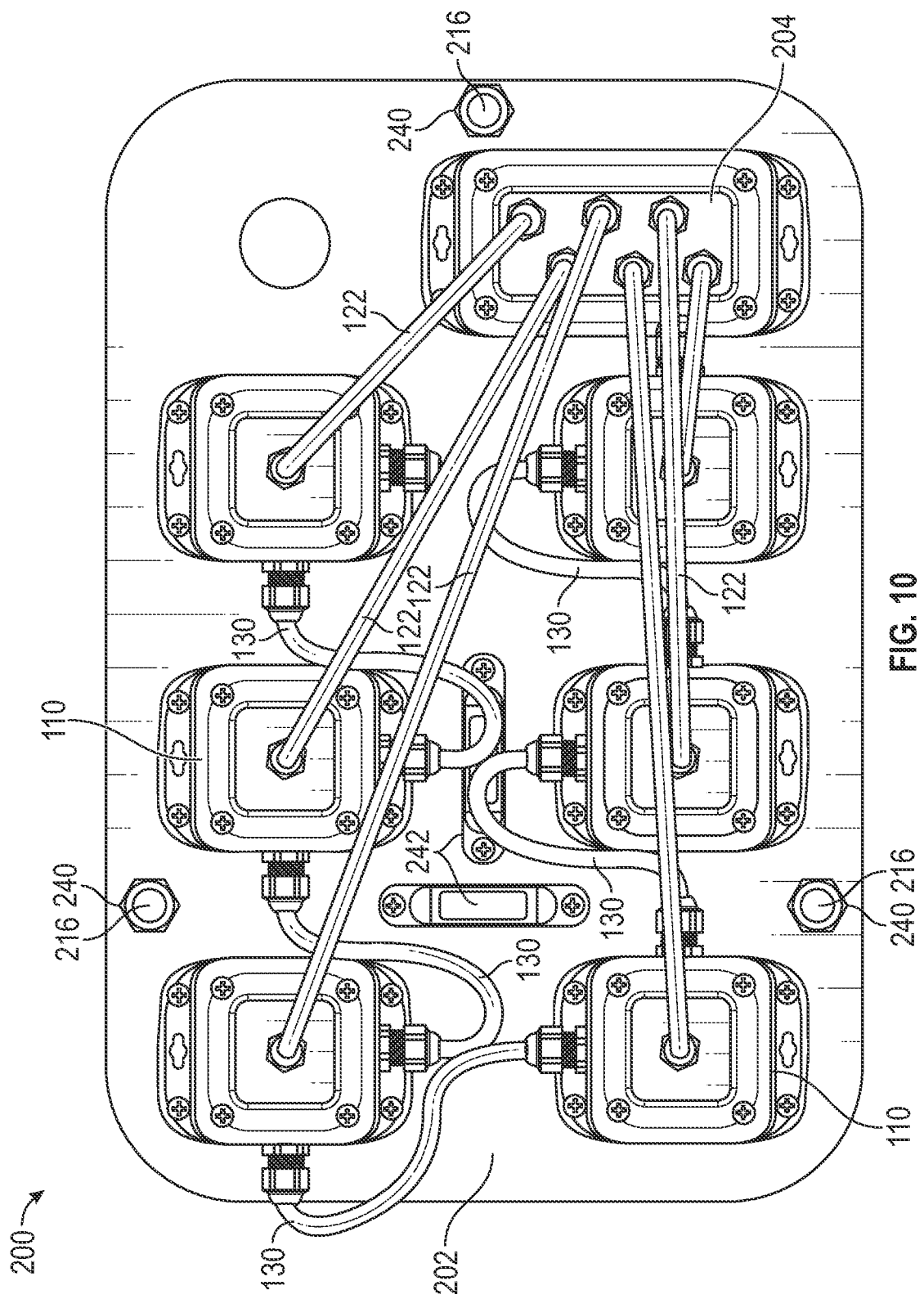
FIG. 10 is a plan view of some of the components depicted in FIG. 8.
Figure 11:
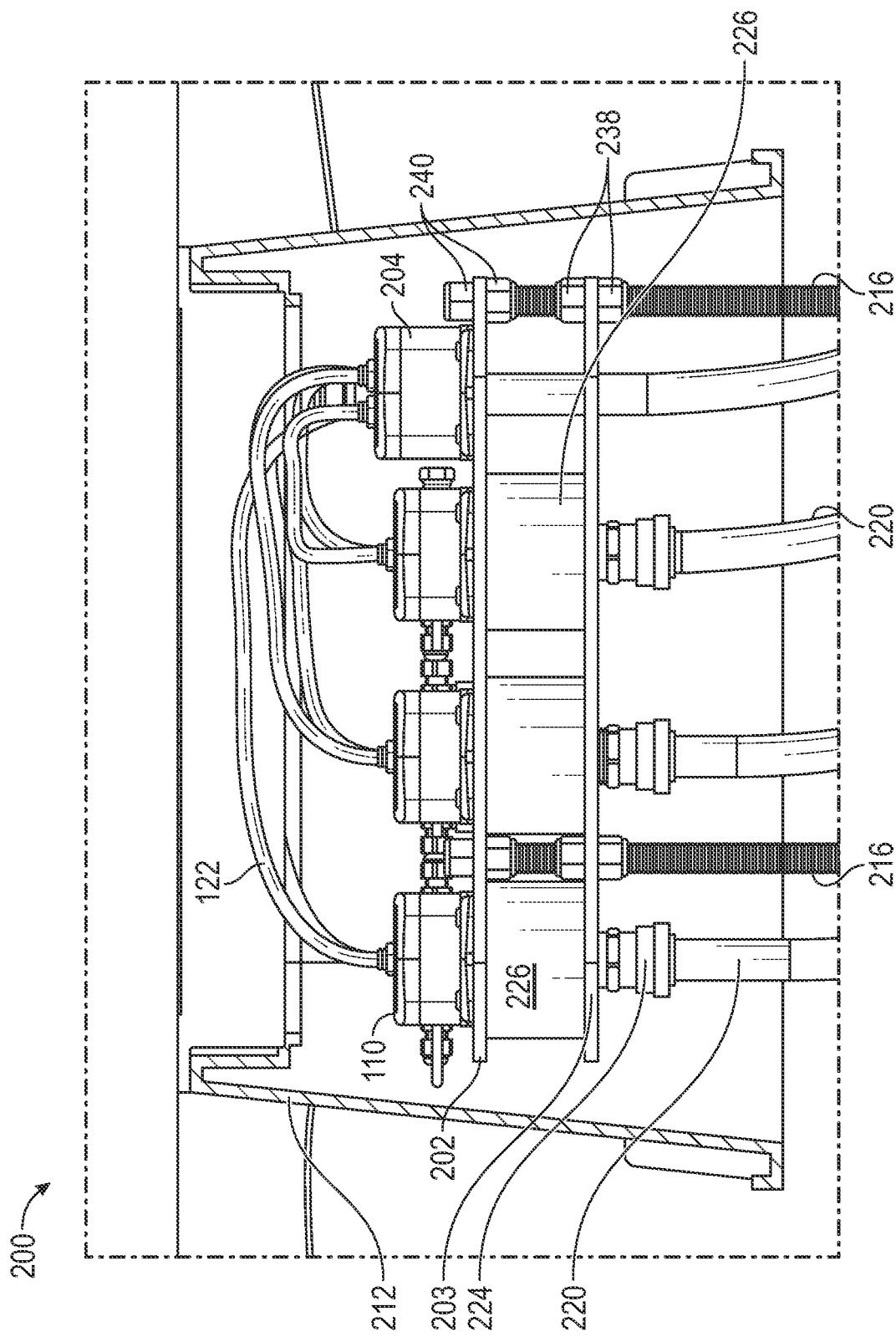
FIG. 11 is an elevation view of some of the components depicted in FIG. 8.

FIG. 10 is a plan view of some of the components depicted in FIG. 8, and FIG. 11 is an elevation view of some of the components depicted in FIG. 8. In some embodiments, it is contemplated that by affixing all sensor heads 110 onto the sensor head base 202, the sensor head base 202 provides a reference point—such as the top surface of the sensor head base 202—for determining the elevation of each sensor 140. Such a reference point can be the same as, or equivalent to, datum 116 for an individual sensor cartridge assembly 100. Additionally, such a reference point is useful if a first (originally installed) sensor cartridge assembly 100 is removed and replaced by a second (replacement) sensor cartridge assembly 100. Such a reference point can provide a consistent comparison basis for data derived from each sensor 140 of both the first and second sensor cartridge assemblies 100. Thus, data derived from sensor(s) 140 of the first sensor cartridge assembly 100 may be readily compared with data derived from sensor(s) 140 of the second cartridge assembly 100.

As illustrated, a first levelling indicator 242 is aligned between two connectors 216, and a second levelling indicator 242 is aligned between the first levelling indicator 242 and a third connector 216. Adjustment of the fasteners 240 while monitoring the levelling indicators 242 enables an operator to configure the sensor head base 202 to be substantially horizontal. Once so leveled, an operator can determine whether the sensor head base 202 continues to remain level, such as by periodic inspection of the levelling indicators 242, or via sensor readings from three or more non-collinear sensor heads 110 mounted on the sensor head base 202. In some embodiments, it is contemplated that an operator may not perform a levelling operation, such as if only a single sensor cartridge assembly 100 is to be installed at the sensor head base 202.

Figure 12:
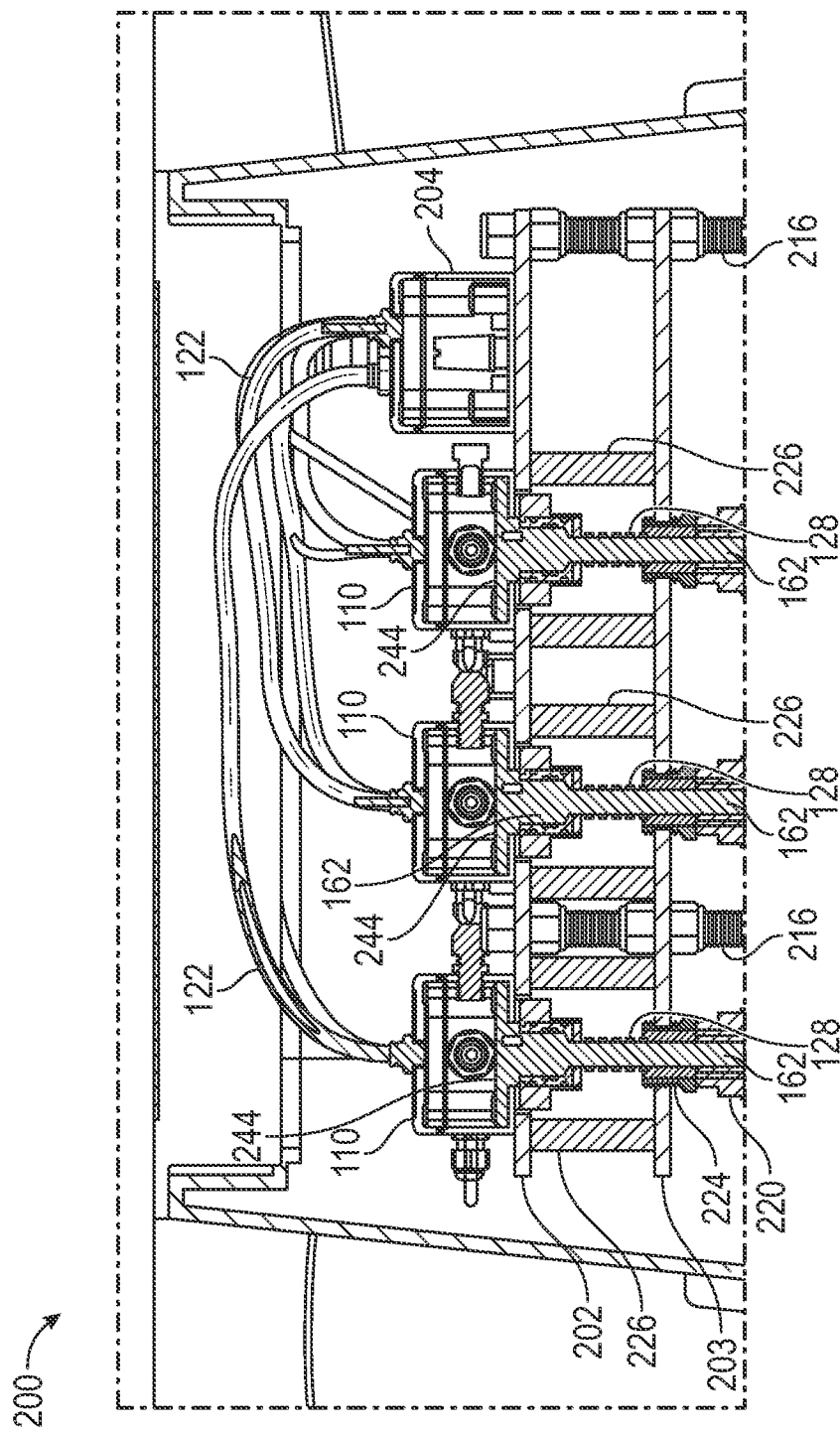
FIG. 12 is a section view of the components depicted in FIG. 11.

FIG. 12 is a section view of the components depicted in FIG. 11. Sensor fluid 162 fills each sensor tube 128 and up to a sensor fluid level 244 within each sensor head 110. In some embodiments, it is contemplated that the sensor fluid level 244 within each sensor head 110 is substantially the same, such as within 0.2 inches (5 mm). In some embodiments, it is contemplated that the sensor fluid level 244 within each sensor head 110 is not substantially the same. In some embodiments, it is contemplated that the sensor fluid level 244 within each sensor head 110 is managed such that a known offset exists between the sensor fluid level 244 in one sensor head 110 and the sensor fluid level 244 in another sensor head 110.

In some embodiments, it is contemplated that the sensor fluid level 244 within each sensor head 110 is above each corresponding sensor 140 within each sensor head 110. The monitoring and adjustment of sensor fluid level 244 may be performed during maintenance. In some embodiments, it is contemplated that anomalous readings from a sensor 140 in a sensor head 110 may indicate that a drop of sensor fluid level 244 below the sensor 140 has occurred. In an example, the anomalous readings may relate to changes in the data obtained from a single sensor 140 over time. In another example, the anomalous readings may relate to changes in the data obtained from a single sensor 140 compared to data obtained from other sensors 140 in other sensor heads 110.

Figure 13:
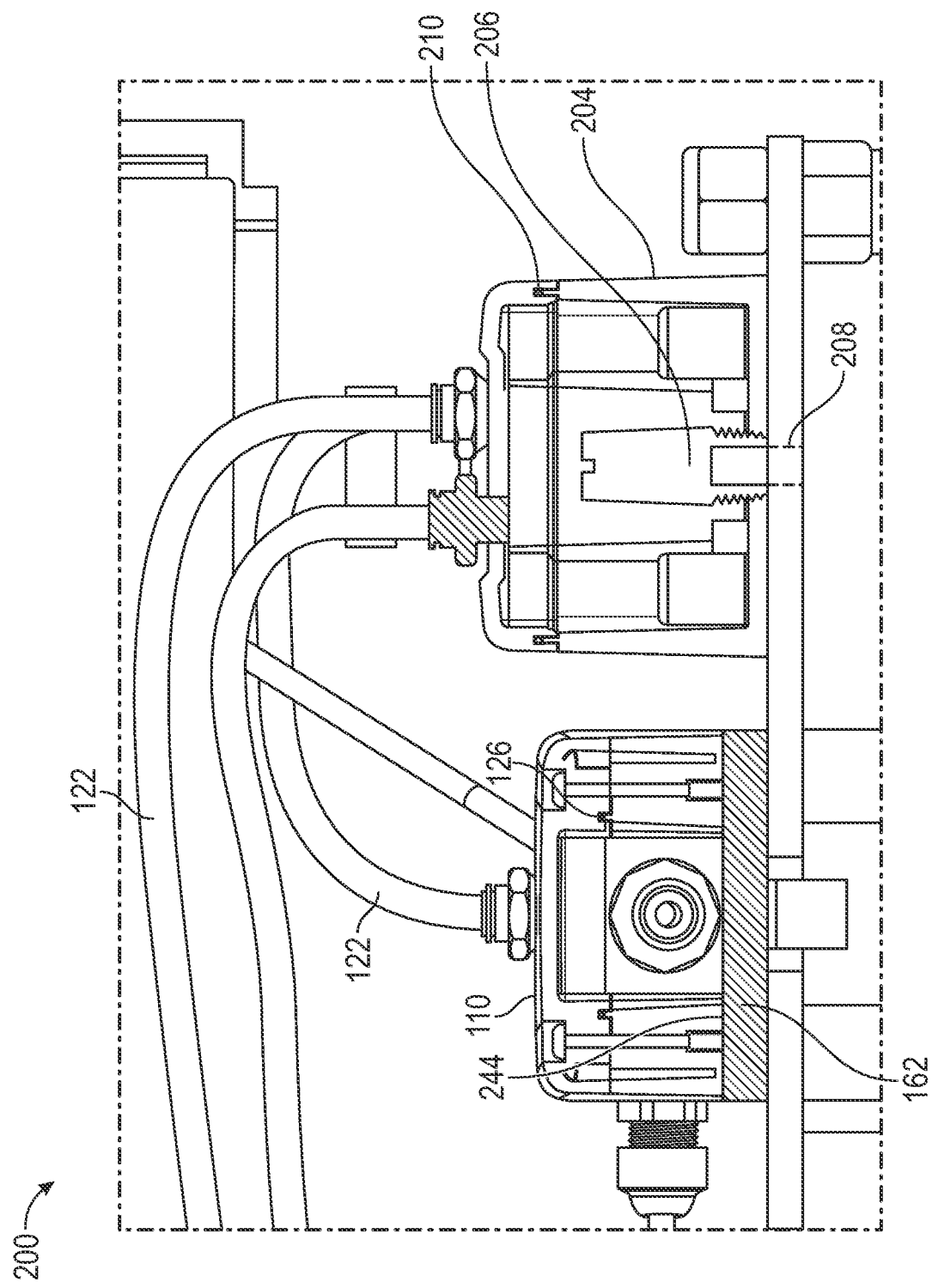
FIG. 13 is a detailed view of a portion of FIG. 12.

FIG. 13 is a detailed view of a portion of FIG. 12. A seal 210 prevents ingress of foreign material and water between component parts of the pressure balance chamber 204. Air pressure acting on the sensor fluid 162 at the sensor fluid level 244 in a sensor head 110 is communicated via pressure balance tube 122 linking the sensor head 110 with the pressure balance chamber 204. A pressure balance passage 208 out of the bottom of the pressure balance chamber 204 and through the sensor head base 202 enables air pressure within the pressure balance chamber 204 to be equalized against atmospheric pressure. A filter 206 inhibits ingress of foreign material, such as dust, debris, organic material (such as plant roots or insects), or other material transported by other contaminating sources such as ants, into the pressure balance chamber 204.

In some embodiments, it is contemplated that the pressure balance passage 208 may include a valve that regulates movement of air through the pressure balance passage 208. In an example, the valve may operate like a float valve in a cistern such that rising water causes the valve to close, thereby inhibiting flood water from entering the pressure balance chamber 204. Similarly, when the water level drops below a predetermined point, the valve may open to reestablish pressure communication between the pressure balance chamber 204 and the atmosphere. In another example, the valve may be actuated to close and open by a controller.

In another embodiment, a diaphragm within the pressure balance chamber 204 separates the air that is communicated through the pressure balance tube(s) 122 from the atmosphere within the container 212. For example, an elastomeric diaphragm may be sufficiently flexible to deform when subject to a pressure difference, but also effect a seal to prevent contamination of the air communicated through the pressure balance tube(s) 122 by foreign material and water.

The above measures assist in preserving the quality of the sensor fluid 162. In an example, the filter 206, seal 210, valve, and/or diaphragm inhibit impurities from being introduced into the sensor fluid 162 that may alter the density or other properties of the sensor fluid 162. In some embodiments, the pressure balance chamber 204 may contain a desiccant.

In some embodiments, it is contemplated that installation of the foundation monitoring system 1000 at a work site includes pre-installing one or more raceway 220 at a foundation. The sensor head base 202, assembly base 203, and anchor base 218 are put in place. In some embodiments, it is contemplated that the sensor head base 202 is then adjusted to be horizontal, such as by manipulation of the fasteners coupling the sensor head base 202 to the connectors 216 (see FIG. 8).

Deployment of a sensor cartridge assembly 100 at a location where there exists a pre-installed raceway 220 involves inserting the sensor tube 128—containing one or more sensor 140 and sensor fluid 162—of the sensor cartridge assembly 110 into the corresponding raceway 220. During insertion of the sensor tube 128 into the corresponding raceway 220, friction between the sensor tube 128 and the raceway 220 can hinder travel of the sensor tube 128 through the raceway 220. In some embodiments, such friction is mitigated by a selection of materials of the raceway 220 and/or of the sensor tube 128. For example, one or both of the sensor tube 128 and/or the raceway 220 may be manufactured from a low friction material, such as a plastic, such as polyvinylchloride or polytetrafluoroethylene. In another example, one or both of the sensor tube 128 and/or the raceway 220 may include a coating of a low friction material, such as polytetrafluoroethylene.

In some embodiments, it is contemplated that the raceway 220 is cleaned prior to inserting the sensor tube 128. In some embodiments, it is contemplated that fluid in the annulus 228 between the raceway 220 and the sensor tube 128 is configured to lubricate the passage of the sensor tube 128 through the raceway 220. In an example, the fluid in the annulus 228 may include a lubricant. In a further example, the fluid in the annulus 228 may be selected to provide a low friction interface between the sensor tube 128 and the raceway 220. For instance, the fluid in the annulus 228 may be a mineral oil. In another example, a lubricant may be added to the exterior of the sensor tube 128 and/or to the interior of the raceway 220. In such embodiments, it is contemplated that the lubricant may be added before and/or during insertion of the sensor tube 128 into the raceway 220. In some embodiments, it is contemplated that the fluid in the annulus 228 may mitigate friction between the sensor tube 128 and the raceway 220 due to buoyancy of the sensor tube 128 in the fluid in the annulus 228.

Deployment of the sensor cartridge assembly 100 continues until the sensor head 110 is positioned close to the sensor head base 202 of the sensor head assembly 200. In embodiments in which the sensor tube 128 is connected to the sensor head 110 via a swivel 138, the swivel 138 allows the sensor head 110 to be rotated relative to the sensor tube 128 as needed to align the mounting fasteners 124 with corresponding mounting points on the sensor head base 202. In embodiments in which the swivel 138 is omitted, the sensor head 110 and the sensor tube 128 are rotated as needed to align the mounting fasteners 124 with corresponding mounting points on the sensor head base 202.

When the sensor head 110 is then lowered and positioned on the sensor head base 202, the mounting fasteners 124 are operated to secure the sensor head 110 to the sensor head base 202. The wiring 130 is interconnected and routed as needed. The seal stem 166 is removed from the sensor head, and the sensor fluid 162 may be topped up as needed such that the sensor 140 within the sensor head 110 becomes submerged in sensor fluid 162. The pressure balance tube 122 is connected to the sensor head 110.

Removal of a sensor cartridge assembly 100 from an installation involves disconnecting the pressure balance tube 122, disconnecting the wiring 130, and disconnecting the mounting fasteners 124. In some embodiments, it is contemplated that the seal stem 166 is reinstalled in the sensor head 110, for example, to prevent loss of sensor fluid 162 via drainage during subsequent removal and transport of the sensor cartridge assembly 100. Removal of the sensor cartridge assembly 100 continues by pulling on the sensor head 110 to cause the sensor tube 128 and all components therein to be withdrawn. Thus, individual sensor cartridge assemblies 100 can be removed and replaced as needed.

In some embodiments, it is contemplated that a raceway 220 may be routed around and/or within a foundation such that there exist multiple bends of the raceway 220. Deployment (and/or retrieval) of the sensor tube 128 within such a raceway 220 may be accomplished by employing one or more friction mitigation measures discussed above. In an example, a single sensor tube 128 may be deployed in a raceway 220 to a total payout distance 158 of more than 350 feet (107 m) and including a number of bends that total 1,440°. Thus, in some embodiments, it is contemplated that the monitoring of some foundations may be accomplished with the installation of a single sensor cartridge assembly 100. Nevertheless, in some embodiments it is contemplated that the monitoring of some foundations may be accomplished with the installation of a plurality of sensor cartridge assemblies 100.

With the ability to push sensor tube 128 around bends in a raceway 220 and achieve long runs, a foundation may be monitored by sensors 140 in a sensor tube 128 that is placed within a raceway 220 mounted to the perimeter of a foundation. The foundation may be newly constructed or pre-existing. As discussed above, the accuracy of the data obtained from the sensors 140 is enhanced by thermally insulating the raceway 220 and sensor tube 128 therein from daily thermal and atmospheric pressure changes, and by placing the raceway 220 below ground level 310. A raceway 220 may be fitted to a perimeter of an existing foundation and/or a perimeter of an existing structure, and sensor tube 128 with sensors 140 may be installed in the raceway 220 in order to provide monitoring of the perimeter of the foundation and/or the perimeter of the structure, respectively. Such an installation may be planned prior to the creation of the foundation and/or the structure. Alternatively, or additionally, such installation may be planned and executed as a retrofit to an existing foundation and/or an existing structure.

Figure 14:
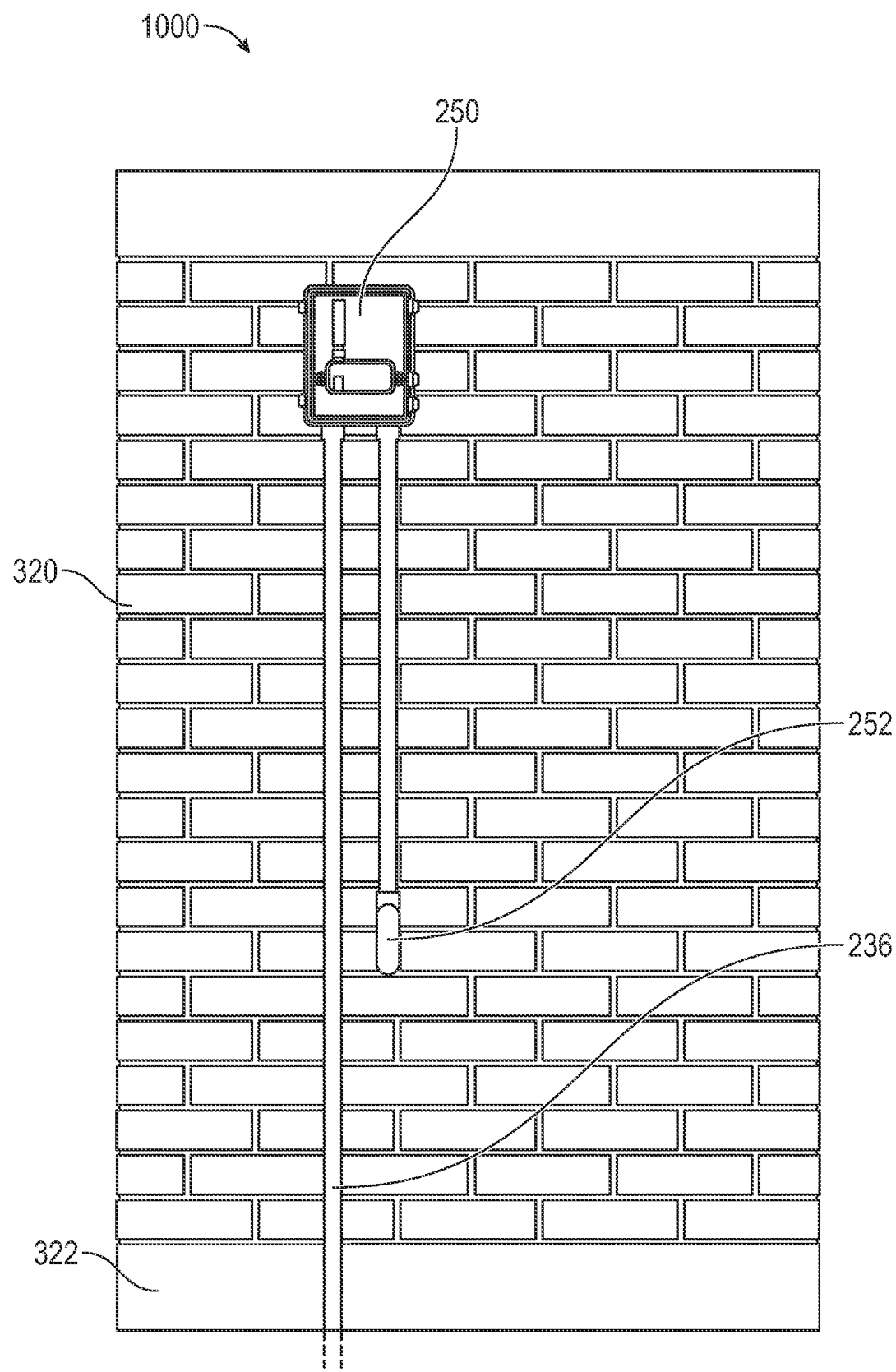
FIG. 14 is an elevation view of a portion of a foundation monitoring system installed on a structure.

FIG. 14 is an elevation view of a portion of foundation monitoring system 1000 installed on a structure. The structure includes a building 320 atop a foundation 322. Wiring 130 from one or more sensor head assembly 200 is routed via electrical raceway 236 to a data transmitter 250. In some embodiments, it is contemplated that the wiring 130 conveys power and/or control signals to the sensors 140 deployed in the foundation monitoring system 1000. In some embodiments, it is contemplated that the wiring 130 conveys sensor data to the data transmitter 250. In some embodiments, it is contemplated that sensor data is conveyed to the data transmitter 250 wirelessly.

In some embodiments, it is contemplated that the data transmitter 250 is an Internet of Things gateway. It is further contemplated that the data transmitter 250 may transmit data via any one or more of a cellular network, an Ethernet cable, Wi-Fi, Bluetooth, or another communication protocol. As illustrated, the data transmitter 250 is powered via a power connection 252, such as to an electrical outlet. In some embodiments, it is contemplated that the data transmitter 250 may be powered by any one or more of an electrical supply to the building, a battery, or a solar panel. The data transmitter 250 receives data from each sensor 140, and conveys the data to a controller, such as a computer.

Figure 15:
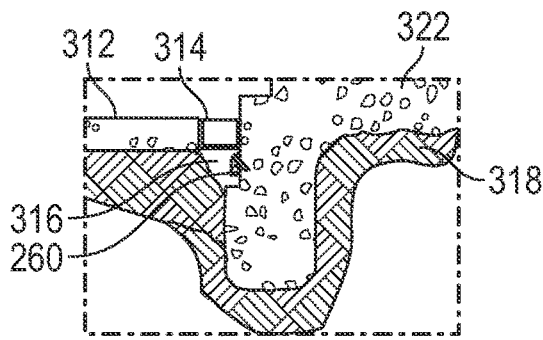
FIGS. 15 to 18 are cross-sectional depictions of alternative deployments of an installation of a portion of a foundation monitoring system.

FIGS. 15 to 18 are cross-sectional depictions of alternative deployments of a portion of an installation of foundation monitoring system 1000. In FIG. 15, a spacer 314 is provided between a foundation 322 and another structure, such as flatwork 312. It is contemplated that the spacer 314 may be any convenient material, such as wood or loose brick, that is removable without disturbing the foundation 322 or the flatwork 312. Beneath the spacer 314, and against the foundation 322, is a provision 316 for a raceway. In some embodiments, it is contemplated that the provision 316 for the raceway is an excavated portion of the ground that has been backfilled with soil, sand, and/or gravel. As illustrated, a raceway anchor 260 is attached to the foundation 322 at the time of constructing the provision 316 for the raceway. In some embodiments, it is contemplated that the raceway anchor may be attached to the foundation at the time when the raceway itself is installed. In the event that a raceway is to be installed against the foundation 322 as a retrofit, the spacer 314 and provision 316 for the raceway are removed. Then a raceway is anchored to the foundation 322 by raceway anchor 260, and the soil, sand, and/or gravel is returned and packed around the raceway. Then the spacer 314 is replaced.

Figure 16:
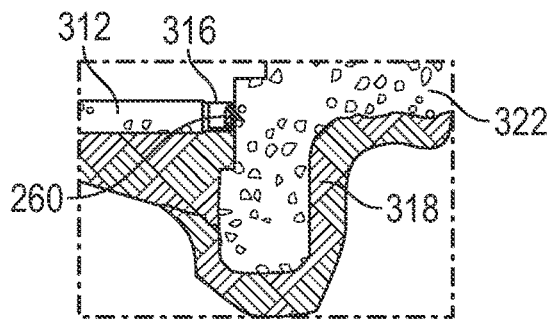

In FIG. 16, a raceway anchor 260 is attached to the foundation 322 at the time of constructing the provision 316 for the raceway. In some embodiments, it is contemplated that the raceway anchor 260 may be attached to the foundation at the time when the raceway itself is installed. In the event that a raceway is to be installed against the foundation 322 as a retrofit, the flatwork 312 (or topsoil, if present) abutting the foundation 322 is removed, and then a raceway is anchored to the foundation 322 by raceway anchor 260. Thereafter, the flatwork 312 is replaced, such as by pouring concrete over the raceway. Alternatively, the topsoil is replaced as desired.

Figure 17:
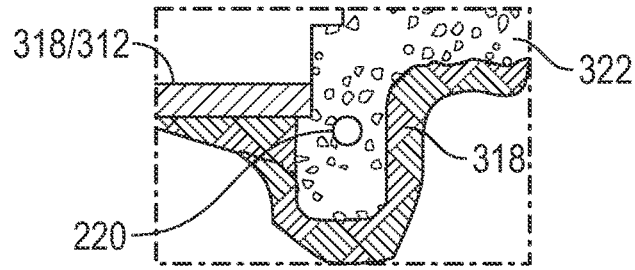

FIG. 17 depicts a raceway 220 placed within the foundation 322. In some embodiments, it is contemplated that at least a portion of the raceway 220 may be installed within the foundation 322, and at least a portion of the raceway 220 may be attached to an external portion of the foundation 322. Thus, sensors 140 installed in such a raceway 220 may be placed within the foundation 322 and along a perimeter of the foundation 322. Additionally, or alternatively, a first raceway 220 may be installed within the foundation, and a second raceway 220 may be attached to an external portion of the foundation 322. Hence, sensors 140 of a first sensor cartridge assembly 100 may be placed within the foundation 322, and sensors 140 of a second sensor cartridge assembly 100 may be placed along a perimeter of the foundation 322.

The placement of sensors 140 within a foundation 322, and optionally at the perimeter of a foundation 322, enables the curing of the concrete of the foundation 322 to be monitored. In some embodiments, it is contemplated that the monitoring may be achieved by sensors 140 at spaced intervals, such as at 10 feet (3 m) intervals, across the foundation 322—centrally and peripherally. Since the curing of concrete is exothermic, the monitoring may include measuring temperatures at each sensor location continuously or at regular time intervals. Thus, a temperature map of the foundation 322 may be created that is akin to a map of the progress of curing over time. Hence, when temperature stabilization is observed, the timing of further work, such as the building of a structure on the foundation 322, may be optimized. It is contemplated that the monitoring of curing at specific locations and then monitoring subsequent vertical movement has particular utility in facilitating improving engineering design guidelines.

Figure 18:
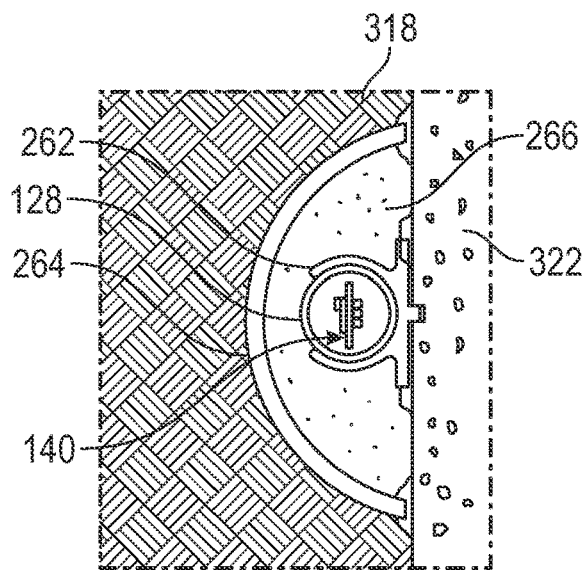

FIG. 18 depicts an embodiment in which a sensor tube 128 is deployed against a foundation 322 without a raceway. Such an embodiment is of utility for short term readings, such as during a real estate transaction to determine the relative movement of a foundation 322 in a matter of weeks or days. The sensor tubing 128 is clipped to a tubing anchor 262 that is attached to the foundation 322. The tubing anchor 262 is attached to the foundation 322 by a fastener, such as a screw that penetrates into the foundation. In some embodiments, it is contemplated that the location of fastening the tubing anchor 262 to the foundation 322 may serve as a reference point for data measured by a sensor 140 in the attached sensor tube 128. Such an installation of a sensor tube 128 enables removal and replacement of the sensor tube 128 despite the lack of a raceway.

A tubing protector 264 is attached to the foundation 322 and covers the sensor tube 128. The tubing protector 264 prevents materials, such as soil, from impacting and distorting or damaging the sensor tube 128. In some embodiments, it is contemplated that thermal insulation 266 may be placed in the tubing protector 264 and around the sensor tube 128. In some embodiments, it is contemplated that the thermal insulation 266 may be omitted. In some embodiments, it is contemplated that the tubing protector 264 may be omitted.

Figure 19:
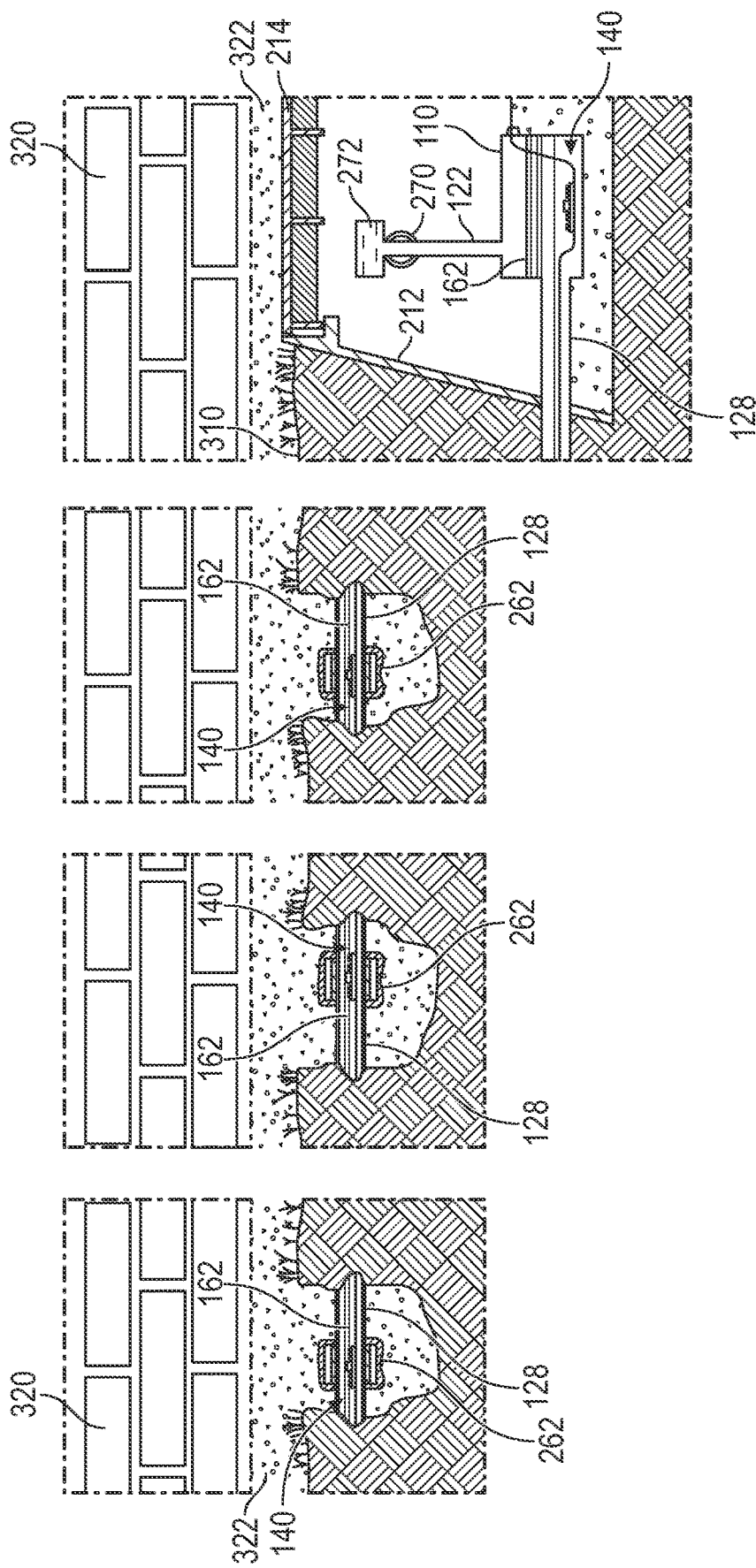
FIG. 19 depicts another embodiment of a foundation monitoring system.

FIG. 19 depicts another embodiment in which a sensor tube 128 is deployed against a foundation 322 without a raceway. Sensor tube 128 containing sensors 140 is attached to the foundation 322 by one or more tubing anchor 262, and is coupled to a sensor head 110 that is disposed below ground level 310 in a container 212, such as utility box. In some embodiments, it is contemplated that the container 212 is fitted with a cover 214, which in the illustrated example is at ground level 310. In some of such embodiments, it is contemplated that the cover 214 may be thermally insulated. In some embodiments, the cover 214 may be omitted. In some embodiments, it is contemplated that at least a portion of the container 212 may be above ground level 310.

As in other embodiments described above, the sensor head 110 contains a sensor 140, and the sensors 140 in the sensor tube 128 and sensor head 110 are immersed in sensor fluid 162. A pressure balance tube 122 from the sensor head 110 includes a valve 270 and a vent 272. In some embodiments, measurements from the sensors 140 are taken when the valve 270 is open in order to prevent buildup of pressure inside the sensor head 110 and sensor tube 128. In some embodiments, the valve 270 is closed while obtaining measurements from the sensors 140. The closed valve 270 isolates the sensor fluid 162 from intrusion of foreign matter (such as air, moisture, and debris), and in the absence of a physical pressure compensation, sensor measurements are corrected as a function of pressure variations inside the closed system of sensor head 110 plus sensor tube 128 as temperatures change. In some embodiments, measurements from the sensors 140 are taken when the valve 270 is open and when the valve 270 is closed. In another embodiment, a fluid cap may be used in place of the valve 270.

In all of the above embodiments, measurements from each sensor 140 are utilized for any one of a variety of assessments of a foundation and/or a structure built upon a foundation. Example structures include, without limitation, buildings, dams, walls, tunnels, bridges, storage tanks, wind turbine, or any other construction upon the Earth's surface. Example assessments include, without limitation, maintenance interval prediction, repair evaluation, performance evaluation of contractors, actuarial data and insurance, intentional stress testing of foundation designs, and comparative performance analysis of foundation designs.

In all of the above embodiments, measurements from each sensor 140 are obtained without moving the sensor 140 from one measurement location to another measurement location in between taking measurements. The sensor 140 is used to acquire measurements over the course of a time period that may be seconds, minutes, hours, days, weeks, months, or years in duration. Measurements from each sensor 140 may be taken whenever necessary. For example, measurements from each sensor 140 may be taken at regular time intervals, such as hourly, daily, weekly, bi-weekly, monthly, bi-monthly, quarterly, semi-annually, annually, etc. In another example, measurements from each sensor 140 are taken continuously or continually over a time period, such as every few seconds or every few minutes.

Each measurement may involve taking a set of readings from a sensor for several seconds, minutes, or hours. Each set of readings may involve taking a reading every second, or every multiple of seconds (such as every two seconds), or every fraction of a second (such as every tenth of a second). An interval between successive measurements may last a number of minutes, a number of hours, a number of days, a number of weeks, a number of months, or a number of years. In an example, readings from each sensor 140 are taken continually over a short time period, such as two minutes, and repeat batches of readings are taken at regular time intervals, such as hourly, daily, weekly, bi-weekly, monthly, bi-monthly, quarterly, semi-annually, annually, etc.

In another example, measurements from each sensor 140 are obtained based on the existence of a predetermined environmental condition, such as an ambient temperature condition, such as a daily low temperature. For instance, readings from each sensor 140 may be obtained continually over a predetermined time period, and correlated against local ambient temperature data. In another example, readings from each sensor 140 are taken continually over a time period such that a stabilization of the readings from individual sensors 140 can be established. Stabilized readings from each sensor 140 can then be selected for analysis.

In some embodiments, it is contemplated that readings from each sensor 140 are deemed to be stabilized when a magnitude of a difference between successive readings, or a standard deviation of a set of readings, is less than or equal to a threshold value, such as 1 psi (0.07 bar) or 1° F. (0.56° C.). Threshold values of other magnitudes are also contemplated, according to a selection by an operator or by an algorithm executed by a controller of the foundation monitoring system 1000. In some embodiments, it is contemplated that the threshold value may be determined as a fraction of the value of a selected reading, such as 10%, 5%, 2%, 1%, or 0.5%.

In some embodiments, it is contemplated that readings from each sensor 140 are deemed to be stabilized when a magnitude of a difference between calculated elevations derived from successive readings, or a standard deviation of calculated elevations derived from each reading of a set of readings, is less than or equal to a threshold value. In an example, readings from each sensor 140 are deemed to be stabilized when a standard deviation of calculated elevations derived from each reading of a set of readings is less than or equal to 0.5 inches (1.27 cm). Threshold values of other magnitudes are also contemplated, according to a selection by an operator or by an algorithm executed by a controller of the foundation monitoring system 1000.

In a further example, readings from each sensor 140 are used to calculate a set of raw elevation values of each sensor 140 with respect to the datum 116. A standard deviation of the set of raw elevation values of each sensor 140 is then determined and compared to a threshold value. In one example, the threshold value 0.5 inches (1.27 cm). Threshold values of other magnitudes are also contemplated, according to a selection by an operator or by an algorithm executed by a controller of the foundation monitoring system 1000. The readings from a particular sensor 140 are determined to be stabilized if the standard deviation of the set of raw elevation values is less than or equal to the threshold value. Additionally, or alternatively, the readings from a plurality of sensors 140 are determined to be stabilized if the standard deviations of the sets of raw elevation values from each sensor 140 is less than or equal to the threshold value.

It is contemplated that derivation of an elevation of a sensor 140 relative to the datum 116 may include a statistical analysis of the raw elevation values calculated for the sensor 140. In an example, the statistical analysis includes calculating a mean of the raw elevation values, such as an arithmetic mean, a weighted mean, a geometric mean, or a harmonic mean.

It is contemplated that any of the above examples of sensor measurement regimes may be combined. It is further contemplated that the data from any of the above examples of sensor measurement regimes may be filtered according to one or more data reliability indicator, such as the values obtained, the stability of the measurements over time, and the like.

Moreover, in some embodiments, it is contemplated that measurements are acquired from any two or more sensors 140 simultaneously. In an example, a set of first readings is obtained from a first sensor 140 over the course of a first time period, such as ten minutes. A set of second readings is acquired from a second sensor 140 over the course of a second time period that at least partially overlaps with the first time period. It is contemplated that the second time period may be coincident with the first time period. It is also contemplated that the second time period may be longer in duration than the first time period. It is also contemplated that the second time period may be shorter in duration than the first time period. The first and second sensors 140 may be included in the same sensor cartridge 100, or may be included in different sensor cartridges 100. In some embodiments, the first and second sensors 140 may be located in the same sensor tube 128. In some embodiments, the first sensor 140 is located in a sensor tube 128, and the second sensor is located in a sensor head 110.

In conventional systems in which a single sensor is moved to a plurality of locations within a tube in order to acquire readings at those locations, environmental changes may occur between the taking of readings from the sensor at the first location and the taking of readings at one or more subsequent locations. Such environmental changes may include changes in ambient temperature or pressure, and can adversely affect the accuracy of any correlation between the data acquired at each location.

In contrast, embodiments described herein facilitate the synchronization of reading acquisition from each sensor 140. Thus, readings from each sensor 140—and hence at each measurement location within each sensor tube 128—may be acquired simultaneously. Additionally, or alternatively, readings from a first sensor 140 may be acquired at a short time interval, such as a few seconds, 30 seconds, one minute, etc., before readings from a second sensor 140 are acquired. By obtaining readings from two or more sensors 140 simultaneously (such as described above), a user is able to acquire data pertaining to a foundation in which any adverse effect of environmental changes during the acquisition of the data is mitigated.

Figure 20:
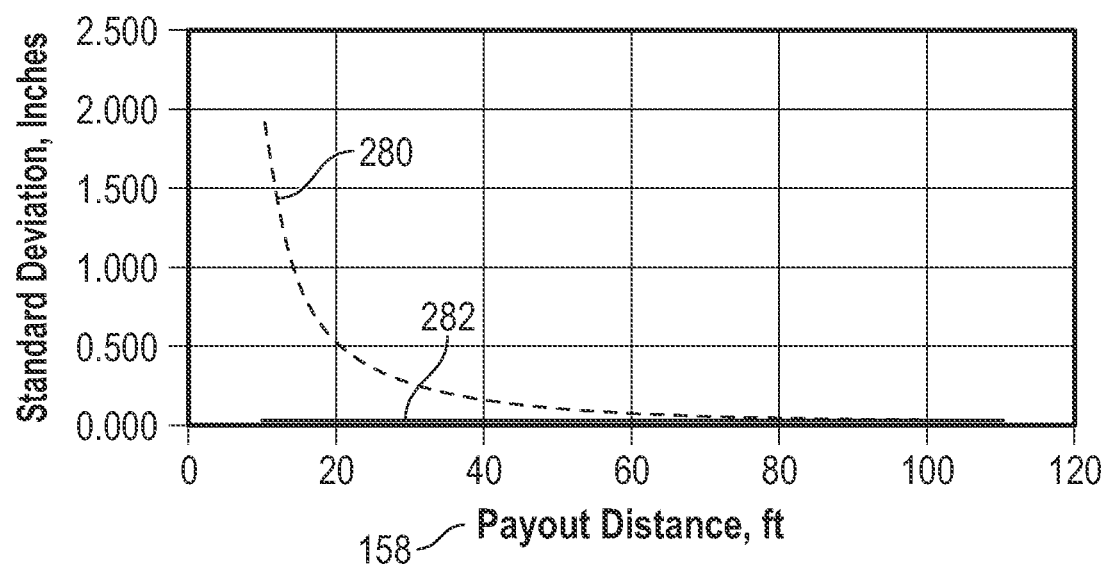
FIG. 20 is a graph illustrating measurement accuracy obtainable by embodiments of the present disclosure in contrast to that obtained by other systems.

FIG. 20 is a graph illustrating an exemplary measurement accuracy obtainable by embodiments of the present disclosure in contrast to that obtained by other systems. The x axis represents the payout distance 158 of each sensor 140 from the reference point datum 116 (referenced in FIG. 2); the y axis represents a standard deviation of measured/derived elevation data produced by the represented systems. The dashed line 280 represents the standard deviation of elevation data produced by a comparative system that involves moving a single sensor within a raceway 220 to a number of measuring stations. The solid line 282 represents the standard deviation of measured/derived elevation data produced by a foundation monitoring system 1000 of the present disclosure.

In the comparative system, a single sensor is placed at a distal end of a tube that is analogous to the sensor tube 128 of the present disclosure. The tube contains a fluid. The tube with the sensor therein is translated inside of a raceway to a first measuring station (at a payout distance 110 ft (33.5 m) in this example). Then, a waiting period (such as 20 minutes) is undertaken to allow for thermal stabilization of the fluid within the tube. At least a portion of the fluid is above ground level 310 in this apparatus, while the raceway and sensor are below ground level 310. Next, once the fluid within the tube has thermally stabilized, a first set of measurements is taken by the sensor. Then the sensor is moved to a second measuring station, such as at a location ten feet (3 m) from the first measuring station. Movement of the sensor to the second measuring station causes hydraulic pressure waves in the fluid within the tube, and may also cause further thermal instability of the fluid within the tube. Because temperature and pressure fluctuations of the fluid within the tube affect the measurements taken by the sensor, another waiting period is undertaken before capturing measurements from the sensor at the second measuring station. The sensor is then moved to successive measuring stations at which the above operations are repeated.

The dashed line 280 represents the standard deviation of elevation data produced by the comparative system. In the example presented, the data was acquired daily over a period of a few months. Although the standard deviations at payout distances from about 40 feet (12 m) to 110 feet (33.5 m) appear acceptable, the standard deviations at payout distances less than about 40 feet (12 m) are unacceptable. It has been determined that the source of the unacceptable standard deviations is thermal in nature, such as resulting from at least a portion of the fluid within the tube being above ground level while another portion of the fluid within the tube is below ground level at the time the measurements are obtained from the sensor. For example, a temperature gradient exists between the different portions of the fluid within the tube, resulting in the fluid within the tube having a density gradient that influences pressure measurements taken by the sensor.

In contrast, embodiments of the foundation monitoring system 1000 of the present disclosure do not suffer from the stability issues of the comparative system. FIG. 20 shows that repeated measurements by an exemplary foundation monitoring system 1000 provide consistently accurate data along an entire length of payout distance 158.

FIG. 20 illustrates that with a system that involves moving a single sensor within a raceway to a number of measuring stations, the standard deviation of elevation data deteriorates markedly with the shorter the length of payout distance. However, with a foundation monitoring system 1000 of the present disclosure, the standard deviation of elevation data is not only as good as that of the comparative system at longer payout distances, but also is maintained even at the shorter payout distances at which the standard deviation of elevation data of the comparative system deteriorates. Thus, embodiments of the present disclosure provide consistently good data accuracy along an entire length of payout distance.

Embodiments of the present disclosure present improvements over current techniques because the need to convey a sensor from one measuring station to another is eliminated. Such improvements include, for example, the elimination of temperature corrections, the elimination of the need for a device to apply a positive pressure to the sensor fluid, the avoidance of gas dissociation in the sensor fluid resulting from movement, and the elimination of error due to the inability to replicate the exact locations of previous readings. Furthermore, embodiments of the present disclosure enable measurements to be obtained even when physical access to individual locations is prevented, such as by flooding.

Embodiments of the present disclosure have utility in the evaluation of foundation movement before, during, and/or after the building of a structure thereon, and for continuing measurement over time. Additionally, embodiments of the present disclosure include an ability to assess the temperature within the foundation to establish such aspects as an acceptable time to begin construction upon a foundation, an unacceptable time at which to avoid beginning construction upon the foundation, and to monitor deflection of the foundation during construction and maintenance.

Embodiments of the present disclosure are useful in evaluating the performance of foundations that do not have a conduit network disposed within the foundations during construction. Further, embodiments of the present disclosure provide methods for evaluating and predicting the utility of foundations that are easier than conventional methods to execute in order to achieve a requisite accuracy.

The systems, apparatus, and methods of the present disclosure may be adapted in many different forms and should not be construed as being limited to the illustrated embodiments set forth herein. It is to be understood further that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation. It is further contemplated that each described embodiment may be combined with one or more other described embodiments.

While the foregoing is directed to embodiments of the present disclosure, other and further embodiments of the disclosure may be devised without departing from the basic scope thereof, which is determined by the claims that follow.

What is claimed is:

1. A foundation monitoring system comprising:
    a sensor cartridge assembly comprising:
        first and second sensors disposed in a sensor tube; and
        a sensor head attached to an end of the sensor tube;
    a raceway configured for attachment to a foundation, wherein the sensor tube is configured to be inserted into the raceway; and
    a data transmitter configured to receive data from the first and second sensors, and convey the data to a controller;
    wherein the controller is configured to acquire simultaneously a first set of temperature and pressure data from the first sensor and a second set of temperature and pressure data from the second sensor.

2. The foundation monitoring system of claim 1, further comprising:
    a third sensor disposed in the sensor head;
    wherein the third sensor is configured to measure temperature and pressure.

3. The foundation monitoring system of claim 2, wherein the sensor cartridge assembly is configured for installation below ground level.

4. The foundation monitoring system of claim 3, wherein the first, second, and third sensors are immersed in a dielectric fluid.

5. A method of monitoring a foundation, comprising:
    acquiring temperature and pressure data from first and second sensors installed within a sensor tube attached to the foundation, wherein:
        the temperature and pressure data includes a first set of temperature and pressure data from the first sensor and a second set of temperature and pressure data from the second sensor; and
        the first and second sets of temperature and pressure data are acquired simultaneously; and
    deriving, from the temperature and pressure data, a first elevation of the first sensor and a second elevation of the second sensor with respect to a predetermined datum.

6. The method of claim 5, wherein:
    the temperature and pressure data includes a third set of temperature and pressure data from the first sensor and a fourth set of temperature and pressure data from the second sensor;
    the third set of temperature and pressure data from the first sensor is acquired after the first set of temperature and pressure data; and
    the fourth set of temperature and pressure data from the second sensor is acquired after the second set of temperature and pressure data.

7. The method of claim 6, wherein the third and fourth sets of temperature and pressure data are acquired simultaneously.

8. The method of claim 5, further comprising determining the temperature and pressure data from the first and second sensors to be stabilized by:
    using the first set of temperature and pressure data to calculate a first set of raw elevation values of the first sensor with respect to the predetermined datum;
    determining a first standard deviation of the first set of raw elevation values;
    using the second set of temperature and pressure data to calculate a second set of raw elevation values of the second sensor with respect to the predetermined datum;
    determining a second standard deviation of the second set of raw elevation values; and
    determining each of the first and second standard deviations is less than or equal to a predetermined threshold.

9. The method of claim 8, wherein the predetermined threshold is 0.5 inches.

10. A method of monitoring a foundation, comprising:
    acquiring temperature and pressure data from first and second sensors installed within a sensor tube attached to the foundation, wherein the temperature and pressure data includes a first set of temperature and pressure data from the first sensor and a second set of temperature and pressure data from the second sensor;
    determining the first and second sets of temperature and pressure data to be stabilized by:
        using the first set of temperature and pressure data to calculate a first set of raw elevation values of the first sensor with respect to a predetermined datum;
        determining a first standard deviation of the first set of raw elevation values;
        using the second set of temperature and pressure data to calculate a second set of raw elevation values of the second sensor with respect to the predetermined datum;
        determining a second standard deviation of the second set of raw elevation values; and
        determining each of the first and second standard deviations is less than or equal to a predetermined threshold; and
    deriving, from the first and second sets of temperature and pressure data, a first elevation of the first sensor and a second elevation of the second sensor with respect to the predetermined datum.

11. The method of claim 10, wherein the predetermined threshold is 0.5 inches.

12. The method of claim 10, wherein:
    the temperature and pressure data includes a third set of temperature and pressure data from the first sensor and a fourth set of temperature and pressure data from the second sensor;
    the third set of temperature and pressure data from the first sensor is acquired after the first set of temperature and pressure data; and
    the fourth set of temperature and pressure data from the second sensor is acquired after the second set of temperature and pressure data.

13. The method of claim 12, wherein the third and fourth sets of temperature and pressure data are acquired simultaneously.

* * * * *